US008148136B1

(12) United States Patent
Hermon-Taylor et al.

(10) Patent No.: US 8,148,136 B1
(45) Date of Patent: Apr. 3, 2012

(54) DIAGNOSTICS AND VACCINES FOR MYCOBACTERIAL INFECTIONS OF ANIMALS AND HUMANS

(75) Inventors: John Hermon-Taylor, London (GB); Timothy John Bull, London (GB)

(73) Assignee: HAV Vaccines Limited, London (GB)

( * ) Notice: Subject to any disclaimer, the term of this patent is extended or adjusted under 35 U.S.C. 154(b) by 0 days.

(21) Appl. No.: 09/646,568

(22) PCT Filed: Mar. 18, 1999

(86) PCT No.: PCT/GB99/00849
§ 371 (c)(1),
(2), (4) Date: Nov. 9, 2000

(87) PCT Pub. No.: WO99/49054
PCT Pub. Date: Sep. 30, 1999

(30) Foreign Application Priority Data

Mar. 20, 1998 (GB) .................................. 9806093.2

(51) Int. Cl.
| C07H 21/04 | (2006.01) |
| C07H 21/02 | (2006.01) |
| C12N 1/12 | (2006.01) |
| C12N 1/20 | (2006.01) |
| C12N 15/00 | (2006.01) |
| A01N 63/00 | (2006.01) |
| A01N 65/00 | (2006.01) |
| A61K 48/00 | (2006.01) |

(52) U.S. Cl. ............... 435/252.3; 435/320.1; 435/253.1; 435/863; 435/864; 536/23.1; 536/23.7; 424/93.1; 424/93.2

(58) Field of Classification Search .................. None
See application file for complete search history.

(56) References Cited

U.S. PATENT DOCUMENTS

| 5,225,324 | A | | 7/1993 | McFadden et al. | |
| 6,156,322 | A | * | 12/2000 | Hermon-Taylor et al. | 424/248.1 |
| 7,541,181 | B2 | | 6/2009 | Hermon-Taylor et al. | |
| 7,758,869 | B2 | * | 7/2010 | Aldwell et al. ............ | 424/234.1 |
| 7,867,704 | B2 | * | 1/2011 | Kapur et al. ................ | 435/6.15 |
| 7,892,566 | B2 | * | 2/2011 | Hermon-Taylor et al. | 424/248.1 |
| 8,003,776 | B2 | * | 8/2011 | James et al. ................ | 536/23.7 |
| 2005/0232937 | A1 | * | 10/2005 | Willemsen et al. ........ | 424/190.1 |
| 2009/0082296 | A1 | * | 3/2009 | James et al. .................... | 514/44 |
| 2009/0203593 | A1 | | 8/2009 | Hermon-Taylor et al. | |
| 2011/0129502 | A1 | * | 6/2011 | Hermon-Taylor et al. | 424/248.1 |

FOREIGN PATENT DOCUMENTS

| EP | 0 288 306 | A | | 10/1998 |
| FR | 2 682 967 | A | | 4/1993 |
| JP | 2009504149 | A7 | * | 2/2009 |
| NZ | 244 901 | | | 7/1995 |
| WO | WO 9501441 | | | 1/1995 |
| WO | WO 97/23624 | | | 7/1997 |
| WO | WO 94/26312 | | | 11/1997 |
| WO | WO 99/49054 | | | 9/1999 |
| WO | WO 2007/017635 | A1 | * | 2/2007 |

OTHER PUBLICATIONS

Li et al, PNAS 2005, 102:12344-12349.*
Motiwala et al, Microbes and Infection, 2006, 8:1406-1418.*
Restifo et al, Gene Therapy, 2000, 7:89-92.*
Leitner et al, Vaccine, 2000, 18:765-777.*
Chemical Abstracts, vol. 74, No. 5, Feb. 1, 1971 Columbus, Ohio, US; abstract No. 20614, Khachaturyan, A. A. et al: "Formation of acylases by hydrocarbon-oxidizing microorganisms" XP002109338 abstract & Biol. Zh. Arm. (1970), 23(7), 40-7.
Belisle, J. T. et al, "Isolation and Expresssion of a Gene Cluster Responsible for Biosynthesis of the Glycopeptidolipid Antigens of *Mycobacterium avium*." J. Bacteriol. 1991, 173: 6991-6997.
Belisle, J. T. et al, "Rough Morphological Variants of *Mycobacterium avium*. Characterization of Genomic Delections Resulting in the loss of Glycopeptidolipid Expression", J. Biological Chem. 1993, 268: 10517-10523.
Mills, J.A. et al, "Loci of *Mycobacterium avium ser2* Gene Cluster and their Functions", J. Bacteriol. 1994, 176:; 4803-4808.
Robison, K., Database EMBL, Entry MT024, Accession No. U00024, Jan. 5, 1995.
Murphy, L., Database EMBL, Entry MTCY277, Accession No. Z79701, Sep. 18, 1996.
Du, L., Database EMBL, Entry MTAD1, Accession No. AD000001, Dec. 15, 1996.
Skelton, J., Database EMBL, Entry MTCY349, Accession No. Z83018, Nov. 26, 1996.
Du, L., Database EMBL, Entry MTAD9, Accession No. AD000009, Dec. 15, 1996.
Vaccine, vol. 12, No. 16, 1994, pp. 1537-1540, XP002026338 Lowrie D B et al: "Towards a DNA Vaccine Against Tuberculosis" see p. 1537-p. 1538.
Nature, vol. 351, No. 6326, Jun. 6, 1991, pp. 456-460, XP000605495 Stover C K et al: "New Use of BCG for Recombinant Vaccines" see p. 456-p. 457.

(Continued)

*Primary Examiner* — Nita M Minnifield
(74) *Attorney, Agent, or Firm* — Nixon & Vanderhye P.C.

(57) ABSTRACT

This invention relates to the protein, *Mycobacterium paratuberculosis* acylase (mpa) and the gene encoding mpa, which we have identified in the pathogen *Mycobacterium paratuberculosis* Mptb (also designated *Mycobacterium avium* subspecies *paratuberculosis* MAP), and to their use in the diagnosis of Mptb/MAP infections in animals and humans, as well as their use as components of vaccines for the prevention and treatment of diseases caused by Mptb/MAP. The importance of an intact uninterrupted mpa gene as a determinant of pathogenicity in Mptb/MAP is recognized and the invention also provides attenuated strains of normally pathogenic Mptb/MAP and other mycobacteria in which mpa has been inactivated, for use as vaccines.

8 Claims, 1 Drawing Sheet

OTHER PUBLICATIONS

Bull et al, "Further studies on the GS element A novel mycobacterial insertion sequence (IS1612), inserted into an acetylase gene (*mpa*) in *Mycobacterium avium* subsp. *silvaticum* but not in *Mycobacterium avium* subsp. *paratuberculosis*", Veterinary Microbiology 77 (2000) 453-463.

Bull et al, "A Novel Multi-Antigen Virally Vectored Vaccine against *Mycobacterium avium* Subspecies *paratuberculosis*", PLoS One, Nov. 2007; 2(11):e1229, pp. 1-14.

Chothia et al, "The relation between the divergence of sequence and structure in proteins", The EMBO Journal, vol. 5, No. 4, pp. 823-826, 1986.

Clark et al, "The *Oac* gene encoding a lipopolysaccharide O-antigen acetylase maps adjacent to the integrase-encoding gene on the genome of *Shigella flexneri* bacteriophage Sf6", Gene, 107 (1991) 43-52.

Cousins et al, "Use of BACTEC radiometric culture method and polymerase chain reaction for the rapid screening of faeces and tissues for *Mycobacterium paratuberculosis*", Australian Veterinary Journal, vol. 72, No. 12, Dec. 1995, pp. 458-462.

Eckstein et al, "A Genetic Mechanism for Deletion of the ser2 Gene Cluster and Formation of Rough Morphological Variants of *Mycobacterium avium*", Journal of Bacteriology, Nov. 2000, vol. 182, No. 21, pp. 6177-6182.

Eckstein et al, "Proposed pathway for the biosynthesis of serovar-specific glycopeptidolipids in *Mycobacterium avium* serovar 2", Microbiology (2003), 149, 2797-2807.

Greenspan et al, "Defining epitopes: It's not as easy as it seems", Commentary—Structural Analysis, 1999 Nature America Inc., http://biotech.nature.com.

Gwozdz et al, "Vaccination against paratuberculosis of lambs already infected experimentally with *Mycobacterium avium* subspecies *paratuberculosis*", Aust Vet J., vol. 78, No. 8, Aug. 2000.

Hermon-Taylor, "Treatment with drugs active against *Mycobacterium avium* subspecies *paratuberculosis* can heal Crohn's diseases: more evidence for a neglected Public Health tragedy", Digest Liver Dis 2002; 34:9-12.

Hermon-Taylor et al, Causation of Crohn's disease by *Mycobacterium avium* subspecies *paratuberculosis*, Can J Gastroenterol, vol. 14, No. 6, Jun. 2000.

Khachaturyan et al, "Formation of acylases by hydrocarbon-oxidizing microorganisms", Chemical Abstracts 74:20614, 1971.

Krzywinska et al, "Characterization of genetic differences between *Mycobacterium avium* subsp. *avium* strains of diverse virulence with a focus on the glycopeptidolipid biosynthesis cluster", Veterinary Microbiology 91 (2003) 249-264.

Meister et al, "Two novel T cell epitope prediction algorithms based on MHC-binding motifs; comparison of predicted and published epitopes from *Mycobacterium tuberculosis* and HIV protein sequences", Vaccine, vol. 13, No. 6, pp. 581-591, 1995.

Mikayama et al, "Molecular cloning and functional expression of a cDNA encoding glycosylation-inhibiting factor", Proc. Natl. Acad. Sci., vol. 90, pp. 10056-10060, Nov. 1993.

Rudinger, "Characteristics of the amino acids as components of a peptide hormone sequence", Peptide Hormones. Biol. Council: 5-7, 1976.

Sasaya et al, "Biological, Serological, and Molecular Variabilities of Clover Yellow Vein Virus", Phytopathology 87:1014-1019, 1997.

Sheridan et al, "Use of Bioinformatics to Predict a Function for the GS Element in *Mycobacterium avium* Subspecies *paratuberculosis*", Journal of Molecular Microbiology and Biotechnology, 2003; 5:57-66.

Tizard et al, "A low G+C content genetic island in *Mycobacterium avium* subsp. *paratuberculosis* and *M. avium* subsp. *silvaticum* with homologous genes in *Mycobacterium tuberculosis*", Microbiology (1998), 144, 3413-3423.

\* cited by examiner

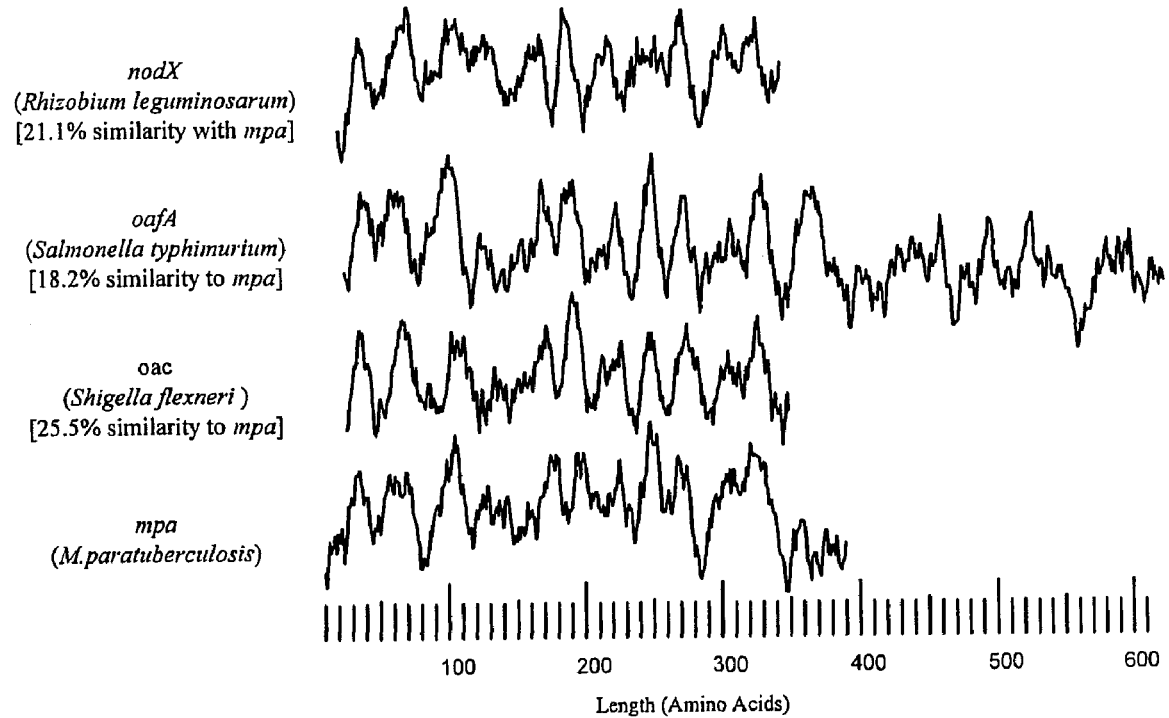

SEQUENCE LISTING

<160> NUMBER OF SEQ ID NOS: 7

<210> SEQ ID NO 1
<211> LENGTH: 1335
<212> TYPE: DNA
<213> ORGANISM: Mycobacterium avium

<400> SEQUENCE: 1

```
gtgactgaag ccaatgagtg caactcggcg tcgcgaaagg tttcagtcgc ggttgagcaa      60
gacaccgcaa gactactgga gtgcgtgcac aagcgccccc agctcgcggc tgaaagcgga     120
tgcaaagggg ttcgaagctt gagcaacatg cgaaggggag aacggcctat gagcctggga     180
caggttttcg acccgcgcgc gaatgcactt aatgcgtggc gcttggtgtt ggcgagcggg     240
gtgatcctat ggcattcgtt tccgctcact ggacgtatgc cgtgggcgcc gttcgtccag     300
ttgcttggcc ttggatgcgt tgatggtttc tttgcggtct ccggctatct catcgtctcg     360
agctggcttc gcaacccgca tcccgcccaa tacttcaccg ctcgatgtct tcgtattctc     420
ccgggtctgt ggatctgtct catcttgacg gcgtttgtca tcgctccgat aggtgtgggc     480
gcccagggcg gttcggccgc gaaactactg atgtccggcg ctccgatcga gtatgtgcta     540
aaagacagtg cggtttggat ggttaagttc gatatcggtg gcacacctcg cgatattcca     600
gttgcgggta tttggaacgg ttctctgtgg acattgggtt gggaggtgct tgctatatc      660 ggcgtagcag tatttggtat gctcggactt cttagtcgcc gttggttcgt tccagggata     720
ttgatcctgg cgctgtcgtg gtcggtgttc ttgccggcat ggggcggaat acacgcgatc     780
gcctccaatg ctgcgcgatt cgctgtgatg tttcggccg gagcgttgct gtatcaattc      840
cgtaacgtga ttccggctcg gtggtccttc gttgccgtcg gcctcattat cgttgtggtt     900
tcctctgccg tgctgccgga ctaccggttg gtggcggccc ttccgatggc gtacctaatc     960
atcgcttcgg gttcgctcat ccacaatcaa aggatgaggt tccgcaccga tctatcctat    1020
ggagtatata tttatgcgtt tccaattcag caagtgctgg tcctgtgtgg attcgccgag    1080
ataaatccaa tcgctttctg cgcgatttct gtcgcagcta ttttgccgct cgccgcgctc    1140
agttggttct tggtcgagaa acctgcgttg tcctggaaga gtcgtctccg gcggaaaaac    1200
agttcaattg cgctagccaa tatggaagat ggtgatcag tcggccgctc aaatgacatt      1260
cccggaaggc gggcccgctt tattggcgag aaagccgaag atcctcccgc gccgagccca    1320
agaccggctt tgtaa                                                     1335
```

<210> SEQ ID NO 2
<211> LENGTH: 444
<212> TYPE: PRT
<213> ORGANISM: Mycobacterium avium

<400> SEQUENCE: 2

-continued

```
Val Thr Glu Ala Asn Glu Cys Asn Ser Ala Ser Arg Lys Val Ser Val
 1               5                  10                 15

Ala Val Glu Gln Asp Thr Ala Arg Leu Leu Glu Cys Val His Lys Arg
            20                  25                  30

Pro Gln Leu Ala Ala Glu Ser Gly Cys Lys Gly Val Arg Ser Leu Ser
        35                  40                  45

Asn Met Arg Arg Gly Glu Arg Pro Met Ser Leu Gly Gln Val Phe Asp
    50                  55                  60

Pro Arg Ala Asn Ala Leu Asn Ala Trp Arg Leu Val Leu Ala Ser Gly
65                  70                  75                  80

Val Ile Leu Trp His Ser Phe Pro Leu Thr Gly Arg Met Pro Trp Ala
                85                  90                  95

Pro Phe Val Gln Leu Leu Gly Leu Gly Cys Val Asp Gly Phe Phe Ala
            100                 105                 110

Val Ser Gly Tyr Leu Ile Val Ser Ser Trp Leu Arg Asn Pro His Pro
        115                 120                 125

Ala Gln Tyr Phe Thr Ala Arg Cys Leu Arg Ile Leu Pro Gly Leu Trp
    130                 135                 140

Ile Cys Leu Ile Leu Thr Ala Phe Val Ile Ala Pro Ile Gly Val Gly
145                 150                 155                 160

Ala Gln Gly Gly Ser Ala Ala Lys Leu Leu Met Ser Gly Ala Pro Ile
                165                 170                 175

Glu Tyr Val Leu Lys Asp Ser Ala Val Trp Met Val Lys Phe Asp Ile
            180                 185                 190

Gly Gly Thr Pro Arg Asp Ile Pro Val Ala Gly Ile Trp Asn Gly Ser
        195                 200                 205

Leu Trp Thr Leu Gly Trp Glu Val Leu Cys Tyr Ile Gly Val Ala Val
    210                 215                 220

Phe Gly Met Leu Gly Leu Leu Ser Arg Arg Trp Phe Val Pro Gly Ile
225                 230                 235                 240

Leu Ile Leu Ala Leu Ser Trp Ser Val Phe Leu Pro Ala Trp Gly Gly
                245                 250                 255

Ile His Ala Ile Ala Ser Asn Ala Ala Arg Phe Ala Val Met Phe Ser
            260                 265                 270

Ala Gly Ala Leu Leu Tyr Gln Phe Arg Asn Val Ile Pro Ala Arg Trp
        275                 280                 285

Ser Phe Val Ala Val Gly Leu Ile Ile Val Val Ser Ser Ala Val
    290                 295                 300

Leu Pro Asp Tyr Arg Leu Val Ala Ala Leu Pro Met Ala Tyr Leu Ile
305                 310                 315                 320

Ile Ala Ser Gly Ser Leu Ile His Asn Gln Arg Met Arg Phe Arg Thr
                325                 330                 335

Asp Leu Ser Tyr Gly Val Tyr Ile Tyr Ala Phe Pro Ile Gln Gln Val
            340                 345                 350

Leu Val Leu Cys Gly Phe Ala Glu Ile Asn Pro Ile Ala Phe Cys Ala
        355                 360                 365

Ile Ser Val Ala Ala Ile Leu Pro Leu Ala Ala Leu Ser Trp Phe Leu
    370                 375                 380

Val Glu Lys Pro Ala Leu Ser Trp Lys Ser Arg Leu Arg Arg Lys Asn
385                 390                 395                 400

Ser Ser Ile Ala Leu Ala Asn Met Glu Asp Gly Gly Ser Val Gly Arg
                405                 410                 415

Ser Asn Asp Ile Pro Gly Arg Arg Ala Arg Phe Ile Gly Glu Lys Ala
```

```
                420              425              430
Glu Asp Pro Pro Ala Pro Ser Pro Arg Pro Ala Leu
        435              440
```

<210> SEQ ID NO 3
<211> LENGTH: 2543
<212> TYPE: DNA
<213> ORGANISM: Mycobacterium avium

<400> SEQUENCE: 3

| | | | | | |
|---|---|---|---|---|---|
| atgcactgtc | aatggccaag | tagaagtccc | cgctggtggc | cagcagaagt | ccccactccg | 60 |
| ctgcgggtgg | ttggctaatt | cttggcggct | cccttcttgt | ggtcggcgtg | gcgcatccgg | 120 |
| taggactcgc | cggaggtgac | gacgatgctg | gcgtggtgca | gcagccgatc | gaggatgctg | 180 |
| gcggcggtgg | tgtgctcggg | caggaatcgc | ccccattgtt | cgaagggcca | atgcgaggcg | 240 |
| atggccaggg | agcggcgctc | gtagccggca | gccacgagcc | ggaacaacag | ttgagtcccg | 300 |
| gtgtcgtcga | gcggggcgaa | gccgatctcg | tccaagatga | ccagatccgc | gcggagcagg | 360 |
| gtgtcgatga | tcttgccgac | ggtgttgtcg | gccaggccgc | ggtagaggac | ctcgatcagg | 420 |
| tcggcggcgg | tgaagtagcg | gactttgaat | ccggcgtgga | cggcagcgtg | cccgcagccg | 480 |
| atgagcaggt | gacttttgcc | cgtaccaggt | gggccaatga | ccgccaggtt | ctgttgtgcc | 540 |
| cgaatccatt | ccaggctcga | caggtagtcg | aacgtggctg | cggtgatcga | cgatccggtg | 600 |
| acgtcgaacc | cgtcgagggt | cttggtgacc | gggaaggctg | cggccttgag | acggttggcg | 660 |
| gtgttggagg | catcgcgggc | agcgatctcg | gcctcaacca | acgtccgcag | gatctcctcc | 720 |
| ggtgtccagc | gttgcgtctt | ggcgacttgc | aacacctcgg | cggcgttgcg | gcgcaccgtg | 780 |
| gccagcttca | accgccgcag | cgccgcgtca | aggtcagcag | ccagcggtgc | cgccgaggac | 840 |
| ggtgccaccg | gcttggcagc | ggtggtcatg | aggccgtccc | gtcggtggtg | ttgatcttgt | 900 |
| aggcctccaa | cgagcgggtc | tcgacggtgg | gcagatcgag | cacgagtgcg | tcgccggcgg | 960 |
| ggcggggttg | tggggtgccg | gcgccggcgg | ccaggatcga | gcgcacgtcg | gcagcgcgga | 1020 |
| accggcgaaa | cgcaaccgcc | cggcgcagcg | cgtcaatcaa | agcctgttcg | ccgtgggcgg | 1080 |
| cgccaaggcc | gagcagaatg | tcgagttcgg | atttcagtcg | ggtgttgccg | atcgcagcag | 1140 |
| caccgacgag | gaactgctgc | gcttcggttc | ccaatgcgca | gaatcgtttc | tctgcttggg | 1200 |
| ttttcgggcg | aggaccacgc | gagggtgcgg | gtctgggtcc | gtcgtagtgt | tcatcgagga | 1260 |
| tggacacctc | acctgggctg | acgagctcgt | gctcggccac | gatcacaccg | gtcgcaggtt | 1320 |
| ccaacaggat | cagggcgcca | tgatcgacca | ccaccgccac | ggtggcaccg | acgagccgct | 1380 |
| gaggcaccga | gtaacgagct | gagccgtaac | ggatgcacga | gaggccgtcg | accttacggc | 1440 |
| gcaccgaccc | cgagccgatc | gtcggccgca | gcgagggcag | ctccctcaag | acggtgcgct | 1500 |
| cgtcaaccaa | gcgatcgttg | ggcacggcgc | agatctccga | gtggaccgtg | gcattgacct | 1560 |
| cggcgcacca | tagttgcgcc | tgggcgttga | gggcacgtag | gtcgacctgc | tcaccggcta | 1620 |
| acgcagcttc | ggtcagcagc | ggcaccgcaa | ggtcgtcctg | agcgtagcca | cagaggttct | 1680 |
| ccacgatgcc | cttcgattgc | ggatccgcac | cgtggcagaa | gtccggaacg | aagccatagt | 1740 |
| gggacgcgaa | tcgcacataa | tccggtgttg | gaacaacaac | attggcgacg | acaccacctt | 1800 |
| tgaggcagcc | catccggtcg | gccaggatct | tggccggaac | cccaccgatc | gcctcgaggg | 1860 |
| cttcggctat | catcgcctgc | gtggtcgagg | ctttctcgtc | ggcggcgaac | cgctcaaacc | 1920 |
| gccaccgcga | ataggccagc | tccgcgcata | acaccatcag | ccccgtgcc | gcttcggccc | 1980 |
| aatccatcac | cagatagtca | ccgggtgacc | agaccgccgg | acggcgttga | tgccggttag | 2040 |

```
cgttgcgcca ccatacttcc tgctcggcta ccaggcggcg gaagttacgg gccgagccct   2100
gatacccggc agctcgggcg atcggcagca tccgcttcgc cgacatcttg ccgtgtgatt   2160
tctcgactcg ggtggcgact agatcggtga acgcgtcgag gttgcgtggc cgtggttccc   2220
gcgggggcgc gccaccggcc tcggcccgct cgatgacccg cttgaccgtc ttgtgcgtac   2280
taccgcacag ctcggccgcg ccgcgatacg acccgacctg gtgatacgcc gaaatgatgt   2340
tcatacgctc ccttgcagac ttcaatagag ctccctgggc ggtgatcaag tgacagttgg   2400
cgctatcacc gtcaccgccc aggccctcag ctcccggaaa agacacgacg agcccgctaa   2460
ggagtgggga cttctacctg gccaccagtg ggacttcct actggccaca gatggggact    2520
ttctcatggc catggacatg cac                                            2543

<210> SEQ ID NO 4
<211> LENGTH: 2543
<212> TYPE: DNA
<213> ORGANISM: Mycobacterium avium

<400> SEQUENCE: 4
gtgcatgtcc atggccatga gaaagtcccc atctgtggcc agtaggaagt ccccactggt     60
ggccaggtag aagtccccac tccttagcgg gctcgtcgtg tcttttccgg gagctgaggg    120
cctgggcggt gacggtgata gcgccaactg tcacttgatc accgcccagg gagctctatt    180
gaagtctgca agggagcgta tgaacatcat ttcggcgtat caccaggtcg ggtcgtatcg    240
cggcgcggcc gagctgtgcg gtagtacgca caagacggtc aagcgggtca tcgagcgggc    300
cgaggccggt ggcgcgcccc cgcgggaacc acggccacgc aacctcgacg cgttcaccga    360
tctagtcgcc acccgagtcg agaaatcaca cggcaagatg tcggcgaagc ggatgctgcc    420
gatcgcccga gctgccgggt atcagggctc ggcccgtaac ttccgccgcc tggtagccga    480
gcaggaagta tggtggcgca acgctaaccg gcatcaacgc cgtccggcgg tctggtcacc    540
cggtgactat ctggtgatgg attgggccga agcggcaccg gggctgatgg tgttatgcgc    600
ggagctggcc tattcgcggt ggcggtttga gcggttcgcc gccgacgaga aagcctcgac    660
cacgcaggcg atgatagccg aagccctcga ggcgatcggt ggggttccgg ccaagatcct    720
ggccgaccgg atgggctgcc tcaaaggtgg tgtcgtcgcc aatgttgttg ttccaacacc    780
ggattatgtg cgattcgcgt cccactatgg cttcgttccg gacttctgcc acggtgcgga    840
tccgcaatcg aagggcatcg tggagaacct ctgtggctac gctcaggacg accttgcggt    900
gccgctgctg accgaagctg cgttagccgg tgagcaggtc gacctacgtg ccctcaacgc    960
ccaggcgcaa ctatggtgcg ccgaggtcaa tgccacggtc cactcggaga tctgcgccgt   1020
gcccaacgat cgcttggttg acgagcgcac cgtcttgagg gagctgccct cgctgcggcc   1080
gacgatcggc tcggggtcgg tgcgccgtaa ggtcgacggc ctctcgtgca tccgttacgg   1140
ctcagctcgt tactcggtgc ctcagcggct cgtcggtgcc accgtggcgg tggtggtcga   1200
tcatggcgcc ctgatcctgt tggaacctgc gaccggtgtg atcgtggccg agcacgagct   1260
cgtcagccca ggtgaggtgt ccatcctcga tgaacactac gacggaccca gacccgcacc   1320
ctcgcgtggt cctcgcccga aaacccaagc agagaaacga ttctgcgcat tgggaaccga   1380
agcgcagcag ttcctcgtcg gtgctgctgc gatcggcaac acccgactga aatccgaact   1440
cgacattctg ctcggccttg gcgccgccca cggcgaacag gctttgattg acgcgctgcg   1500
ccgggcggtt gcgtttcgcc ggttccgcgc tgccgacgtg cgctcgatcc tggccgccgg   1560
cgccggcacc ccacaacccc gccccgccgg cgacgcactc gtgctcgatc tgcccaccgt   1620
```

```
cgagacccgc tcgttggagg cctacaagat caacaccacc gacgggacgg cctcatgacc   1680
accgctgcca agccggtggc accgtcctcg gcggcaccgc tggctgctga ccttgacgcg   1740
gcgctgcggc ggttgaagct ggccacggtg cgccgcaacg ccgccgaggt gttgcaagtc   1800
gccaagacgc aacgctggac accggaggag atcctgcgga cgttggttga ggccgagatc   1860
gctgcccgcg atgcctccaa caccgccaac cgtctcaagg ccgcagcctt cccggtcacc   1920
aagaccctcg acgggttcga cgtcaccgga tcgtcgatca ccgcagccac gttcgactac   1980
ctgtcgagcc tggaatggat tcgggcacaa cagaacctgg cggtcattgg cccacctggt   2040
acgggcaaaa gtcacctgct catcggctgc gggcacgctg ccgtccacgc cggattcaaa   2100
gtccgctact tcaccgccgc cgacctgatc gaggtcctct accgcggcct ggccgacaac   2160
accgtcggca agatcatcga caccctgctc cgcgcggatc tggtcatctt ggacgagatc   2220
ggcttcgccc cgctcgacga caccgggact caactgttgt tccggctcgt ggctgccggc   2280
tacgagcgcc gctccctggc catcgcctcg cattggccct tcgaacaatg ggggcgattc   2340
ctgcccgagc acaccaccgc cgccagcatc ctcgatcggc tgctgcacca cgccagcatc   2400
gtcgtcacct ccggcgagtc ctaccggatg cgccacgccg accacaagaa gggagccgcc   2460
aagaattagc caaccacccg cagcggagtg ggacttctg ctggccacca gcggggactt    2520
ctacttggcc attgacagtg cat                                           2543
```

<210> SEQ ID NO 5
<211> LENGTH: 526
<212> TYPE: PRT
<213> ORGANISM: Mycobacterium avium

<400> SEQUENCE: 5

```
Val Ser Phe Pro Gly Ala Glu Gly Leu Gly Gly Asp Gly Asp Ser Ala
1               5                   10                  15

Asn Cys His Leu Ile Thr Ala Gln Gly Ala Leu Leu Lys Ser Ala Arg
            20                  25                  30

Glu Arg Met Asn Ile Ile Ser Ala Tyr His Gln Val Gly Ser Tyr Arg
        35                  40                  45

Gly Ala Ala Glu Leu Cys Gly Ser Thr His Lys Thr Val Lys Arg Val
    50                  55                  60

Ile Glu Arg Ala Glu Ala Gly Gly Ala Pro Pro Arg Glu Pro Arg Pro
65                  70                  75                  80

Arg Asn Leu Asp Ala Phe Thr Asp Leu Val Ala Thr Arg Val Glu Lys
                85                  90                  95

Ser His Gly Lys Met Ser Ala Lys Arg Met Leu Pro Ile Ala Arg Ala
            100                 105                 110

Ala Gly Tyr Gln Gly Ser Ala Arg Asn Phe Arg Arg Leu Val Ala Glu
        115                 120                 125

Gln Glu Val Trp Trp Arg Asn Ala Asn Arg His Gln Arg Arg Pro Ala
    130                 135                 140

Val Trp Ser Pro Gly Asp Tyr Leu Val Met Asp Trp Ala Glu Ala Ala
145                 150                 155                 160

Pro Gly Leu Met Val Leu Cys Ala Glu Leu Ala Tyr Ser Arg Trp Arg
                165                 170                 175

Phe Glu Arg Phe Ala Ala Asp Glu Lys Ala Ser Thr Thr Gln Ala Met
            180                 185                 190

Ile Ala Glu Ala Leu Glu Ala Ile Gly Gly Val Pro Ala Lys Ile Leu
        195                 200                 205
```

-continued

Ala Asp Arg Met Gly Cys Leu Lys Gly Gly Val Val Ala Asn Val Val
210                 215                 220

Val Pro Thr Pro Asp Tyr Val Arg Phe Ala Ser His Tyr Gly Phe Val
225                 230                 235                 240

Pro Asp Phe Cys His Gly Ala Asp Pro Gln Ser Lys Gly Ile Val Glu
            245                 250                 255

Asn Leu Cys Gly Tyr Ala Gln Asp Asp Leu Ala Val Pro Leu Leu Thr
        260                 265                 270

Glu Ala Ala Leu Ala Gly Glu Gln Val Asp Leu Arg Ala Leu Asn Ala
    275                 280                 285

Gln Ala Gln Leu Trp Cys Ala Glu Val Asn Ala Thr Val His Ser Glu
290                 295                 300

Ile Cys Ala Val Pro Asn Asp Arg Leu Val Asp Glu Arg Thr Val Leu
305                 310                 315                 320

Arg Glu Leu Pro Ser Leu Arg Pro Thr Ile Gly Ser Gly Ser Val Arg
                325                 330                 335

Arg Lys Val Asp Gly Leu Ser Cys Ile Arg Tyr Gly Ser Ala Arg Tyr
            340                 345                 350

Ser Val Pro Gln Arg Leu Val Gly Ala Thr Val Ala Val Val Val Asp
        355                 360                 365

His Gly Ala Leu Ile Leu Leu Glu Pro Ala Thr Gly Val Ile Val Ala
    370                 375                 380

Glu His Glu Leu Val Ser Pro Gly Glu Val Ser Ile Leu Asp Glu His
385                 390                 395                 400

Tyr Asp Gly Pro Arg Pro Ala Pro Ser Arg Gly Pro Arg Pro Lys Thr
                405                 410                 415

Gln Ala Glu Lys Arg Phe Cys Ala Leu Gly Thr Glu Ala Gln Gln Phe
            420                 425                 430

Leu Val Gly Ala Ala Ile Gly Asn Thr Arg Leu Lys Ser Glu Leu
        435                 440                 445

Asp Ile Leu Leu Gly Leu Gly Ala Ala His Gly Glu Gln Ala Leu Ile
    450                 455                 460

Asp Ala Leu Arg Arg Ala Val Ala Phe Arg Arg Phe Arg Ala Ala Asp
465                 470                 475                 480

Val Arg Ser Ile Leu Ala Ala Gly Ala Gly Thr Pro Gln Pro Arg Pro
                485                 490                 495

Ala Gly Asp Ala Leu Val Leu Asp Leu Pro Thr Val Glu Thr Arg Ser
            500                 505                 510

Leu Glu Ala Tyr Lys Ile Asn Thr Thr Asp Gly Thr Ala Ser
        515                 520                 525

<210> SEQ ID NO 6
<211> LENGTH: 23
<212> TYPE: DNA
<213> ORGANISM: Artificial Sequence
<220> FEATURE:
<223> OTHER INFORMATION: Mpa specific primer (P12)

<400> SEQUENCE: 6
agcgagctca cgtgactgaa gcc                                            23

<210> SEQ ID NO 7
<211> LENGTH: 23
<212> TYPE: DNA
<213> ORGANISM: Artificial Sequence
<220> FEATURE:
<223> OTHER INFORMATION: Mpa specific primer (P13)

```
<400> SEQUENCE: 7
gctctgcagc cggaacacaa cgc                                    23
```

DIAGNOSTICS AND VACCINES FOR MYCOBACTERIAL INFECTIONS OF ANIMALS AND HUMANS

This application is a 371 U.S. national phase of International Application No. PCT/GB99/00849, filed Mar. 18, 1999, which designated the U.S. and claims benefit of GB 9806093.2, filed Mar. 20, 1998.

This invention relates to the protein, *Mycobacterium paratuberculosis* acylase (mpa) and the gene encoding mpa, which we have identified in the pathogen *Mycobacterium paratuberculosis* Mptb (also designated *Mycobacterium avium* subspecies *paratuberculosis* MAP), and to their use in the diagnosis of Mptb/MAP infections in animals and humans, as well as their use as components of vaccines for the prevention and treatment of diseases caused by Mptb/MAP. We recognise the importance of an intact uninterrupted mpa gene as a determinant of pathogenicity in Mptb/MAP. Thus the invention also provides attenuated strains of normally pathogenic Mptb/MAP and other mycobacteria in which mpa has been inactivated, for use as vaccines. In the remainder of this specification the abbreviation MAP will be used to denote the pathogen *Mycobacterium paratuberculosis* (*Mycobacterium avium* subspecies *paratuberculosis*). The skilled person would clearly appreciate that the abbreviations MAP and Mptb can be used interchangeably.

MAP is a pathogenic mycobacterium and a member of the group of mycobacteria called *M. avium*-intracellulare (MAIC). MAP causes Johne's disease, a chronic inflammation of the intestine of a broad range of different types in many species of animals including primates. MAP also causes Crohn's disease in humans and other chronic inflammatory diseases such as sarcoidosis. Johne's disease is widespread in Europe and North America as well as elsewhere, and is a major problem in both domestic and wild animals causing substantial economic losses. Crohn's disease in humans is increasing in frequency in Western Europe, North America and elsewhere, and is a major cost to health services.

The diagnosis, prevention and treatment of MAP infections present major problems for veterinary and human medicine, as well as for public health. The development of effective new diagnostics and vaccines for the recognition, prevention and/or treatment of MAP disease, depend upon identifying specific genes and their products within MAP that are both highly specific to MAP and associated with pathogenicity. MAP is very similar to other non-pathogenic members of the MAIC, but some of its genes such as IS900 and the genes of the GS element, are known to be specific or highly selective for this organism and are associated with pathogenicity. Thus, IS900 and GS element polynucleotides and polypeptides are useful in diagnosis and as components of vaccines against MAP.

We have now identified a new gene which occurs naturally within the genome of MAP and which encodes a new protein, mpa. This is termed the mpa gene of the invention. The nucleotide sequence of the mpa gene is given in SEQ ID No. 1 and the amino acid sequence of the mpa polypeptide it encodes is given in SEQ ID No. 2. The uninterrupted mpa gene is specific for MAP. Unlike the genes in the GS element, homologues of the mpa gene are not present in pathogenic *Mycobacterium tuberculosis*. Furthermore, we have found that the equivalent gene to mpa in the closely related but less pathogenic *M. avium* subsp. *silvaticum* (Mays) and *M. avium* TMC724 ATCC 25291 is interrupted by the presence of an IS21— like insertion sequence, IS1612. The nucleotide sequence of IS1612 is given in SEQ ID No. 3 and its complement in SEQ ID No. 4. Nucleotides 1856-2543 of SEQ ID No. 3 and nucleotides 1-688 of SEQ ID No. 4 are new and constitute further aspects of the invention. All or part of the polynucleotide sequence of IS1612 may be used to deactivate mpa in MAP.

We have found that the mpa gene encodes a polypeptide (SEQ ID No. 2) whose function is to acylate or acetylate cell wall components, particularly fucose sugars, in MAP. More precisely mpa functions in conjunction with the five polypeptides encoded by the ORFs present in the GS region of MAP. The five polypeptides encoded by the GS are: gsa a sugar transferase, gsbA and gsbB which function in tandem to produce fucose, gsc a methylase, and gsd a fucosyl transferase. These five polypeptides of GS serve to provide glycosyl peptidolipids (GPL) which comprise a fucosyl moiety and which are located in the mycobacterial cell wall. The methylase gsc acts to methylate, among other groups, the fucosyl moiety of the GPL making it less recognisable by the host's immune system. The acylase, mpa, acts as an acetylating agent on, among other groups, the fucosyl moiety. Acetylation of this GPL broadens the range of animals and host cells which can be infected by MAP.

Acetylation of surface polysaccharides is important in host cell recognition. For example, it is known that de-acetylation of the terminal fucose of GPL's from *M. avium* MAC serotype 9 abolishes rabbit anti-serotype 9 antibody agglutination indicating that acetylation plays a key role in strain variability amongst bacteria and may be directly attributable as a virulence factor. Acetylation of rhamnose in GPL's of *Mycobacterium smegmatis* confers resistance to mycobacteriophage D4 by inducing conformational changes that destroy the phage attachment site. In MAP, the mpa gene is responsible for modification of terminal sugar residues in MAP GPL's which are critically important in determining cell surface recognition and receptor binding and are important determinants of pathogenicity.

Acetylation of LPS's is also known to be critical in destroying antibody epitopes in *S. typhimurium* (Slauch J. M., Lee A. A., Mahan M. J., Mekalanos J. J., J. Bacteriol. 1996, 178, 5904-5909).

Furthermore, acetylation of LPS's is known to increase the virulence of bacteria such as *S. flexneri* (Clark C. A., Beltrame J. and Manning P. A., Gene 1991, 107, 43-52).

Due to its specificity to MAP and some pathogenic *M. avium* ser2, and the involvement of mpa in the biosynthesis and modification of cell wall components, mpa polypeptide can be used as a target for immunodiagnostic tests for the recognition of MAP infections in animals and humans. Furthermore, immunisation of animals or humans with mpa-derived products such as naked mpa DNA in suitable expression constructs, or mpa polypeptide or fragments thereof with adjuvants and carriers, will enhance the immunological resistance of animals and humans to MAP infections. Specific fragments of mpa polypeptide which are particularly suitable targets for diagnostic tests and peptide vaccines can be selected by structural analysis using computer programs well known in the art It is also an objective of the present invention to provide new methods for diagnosing Johne's disease in animals and Crohn's disease in humans using immunoassays based on antibody and cell mediated immune reactivity to mpa or fragments thereof. It is a further objective of the present invention to prevent and/or treat MAP infections in animals and humans by vaccination using the polynucleotides or polypeptides of the mpa gene either alone or together with other polynucleotides and polypeptides associated with pathogenicity, such as those of GS and IS900 known in the art. We recognise that vaccination using naked mpa DNA together with naked GS DNA both in suitable expression constructs will result in the provision of GPL structures on the cell surface of suitable recipient cells, which GPL will resemble those of MAP resulting in the generation of protective immunity. We further recognise that attenuated mutants of MAP provided by interruption or deletion of the mpa gene will be suitable for use as vaccines.

Accordingly, the present invention provides a polynucleotide encoding a protein that comprises *mycobacterium paratuberculosis* acylase (mpa), or a fragment or homologue thereof having mpa activity.

The invention also provides a polynucleotide selected from:
(a) a polynucleotide comprising the nucleotide sequence set out in SEQ ID No. 1 or the complement thereof;
(b) a polynucleotide comprising a nucleotide sequence capable of hybridising to a fragment of the nucleotide sequence set out in SEQ ID No. 1, the fragment having the nucleotide sequence of nucleotides 210-1335 of SEQ ID No. 1;
(c) a polynucleotide comprising a nucleotide sequence capable of hybridising to the complement of a fragment of the nucleotide sequence set out in SEQ ID No. 1, the fragment having the nucleotide sequence of nucleotides 210-1335 of SEQ ID No. 1;
(d) a polynucleotide comprising a polynucleotide sequence which is degenerate as a result of the genetic code to the polynucleotide of SEQ ID No. 1 or a polynucleotide of (c); and
(e) a polynucleotide having at least 80% homology to the nucleotide sequence of SEQ ID No. 1.

The polynucleotide preferably encodes a polypeptide having mpa activity.

The invention also provides a polynucleotide probe or primer which comprises a fragment of at least 15 nucleotides of a polynucleotide selected from:
(b) a polynucleotide comprising a nucleotide sequence capable of hybridising to a fragment of the nucleotide sequence set out in SEQ ID No. 1, the fragment having the nucleotide sequence of nucleotides 210-1335 of SEQ ID No. 1;
(c) a polynucleotide comprising a nucleotide sequence capable of hybridising to the complement of a fragment of the nucleotide sequence set out in SEQ ID No. 1, the fragment having the nucleotide sequence of nucleotides 210-1335 of SEQ ID No. 1; and
(d') a polynucleotide comprising a polynucleotide sequence which is degenerate as a result of the genetic code to a polynucleotide sequence of (c).

The invention also provides a polypeptide encoded by a polynucleotide of the invention, which is not in its natural environment and is preferably in substantially isolated form.

The invention also provides a polypeptide which is not in its natural environment and is preferably in substantially isolated form, which comprises the sequence set out in SEQ ID No. 2, or a polypeptide substantially homologous thereto which has mpa activity, or a fragment of the polypeptide of SEQ ID No. 2 which has mpa activity. The invention also provides a polypeptide comprising at least 8 amino acids which is an immunogenic fragment of said polypeptides and which comprises an epitope. Preferred polypeptides comprise amino acid residues 158-211 and 380-444 of SEQ ID No. 2.

The invention also provides a vector comprising a polynucleotide of the invention. Preferably the vector is an expression vector comprising a polynucleotide of the invention operably linked to regulatory sequences capable of directing expression of said polynucleotide in a host cell. The invention also provides an antibody capable of recognising a polypeptide of the invention including preferred polypeptides. Preferably an antibody which is a monoclonal antibody or a fragment thereof.

The invention also provides a method for detecting the presence or absence of a polynucleotide of the invention in a biological sample which method comprises:
(a) bringing a biological sample containing DNA or RNA into contact with a probe of the invention under hybridising conditions; and
(b) detecting any duplex formed between the probe and nucleic acid in the sample.

The invention also provides a method of detecting the presence or absence of a polypeptide of the invention in a biological sample which method comprises:
(a) incubating the biological sample with an antibody of the invention under conditions which allow for the formation of an antibody-antigen complex; and
(b) determining whether antibody-antigen complex comprising said antibody is formed.

In such a method a substance which is capable of binding the polypeptide of the invention in a specific manner could be used instead of the antibody, and thus (b) would comprise determining whether a complex was formed between the substance and the polypeptide of the invention.

The invention also provides a method of detecting the presence or absence of antibodies to a polypeptide of the invention in a biological sample which method comprises:
(a) incubating a biological sample with a polypeptide of the invention comprising an epitope under conditions which allow for the formation of an antibody-antigen complex; and
(b) determining whether an antibody-antigen complex comprising said polypeptide is formed.

The invention also provides use of a polypeptide of the invention to detect the presence or absence of cell-mediated immune reactivity in an animal or human to the polypeptide. Typically such a method comprises contacting the polypeptide with an immune cell from the human or animal in order to determine the presence or absence of a cellular immune response. In particular the invention provides a method of detecting the presence or absence of cell mediated immune reactivity in an animal or human, to a polypeptide of the invention which method comprises:
(a) incubating a cell sample with a polypeptide of the invention comprising an epitope under conditions which allow for a cellular immune response; and
(b) detecting the presence of said cellular immune response in the incubate.

The invention also provides a test kit for detecting the presence or absence of a pathogenic mycobacterium in a sample which comprises a polynucleotide, a polypeptide or an antibody of the invention.

The invention also provides a pharmaceutical composition comprising (i) a polypeptide, a polynucleotide or an antibody of the invention and (ii) a suitable carrier or diluent.

The invention also provides a polypeptide, a polynucleotide or an antibody of the invention for use in the treatment, prevention or diagnosis of a disease caused by a mycobacterium.

The invention also provides a method of treating or preventing a mycobacterial disease in an animal or human caused by mycobacteria which express a polypeptide of the invention which method comprises administering to the animal or human an effective amount of said polypeptide.

The invention also provides a method of treating or preventing a mycobacterial disease in animals or humans caused by mycobacteria containing the nucleotide sequence of SEQ ID No. 1, which method comprises administering to the animal or human an effective amount of a polynucleotide or a vector of the invention.

Preferably the methods of treating mycobacterial disease of the invention are used against Johne's disease or Crohn's disease.

The invention also provides a method for increasing the in vivo susceptibility of mycobacteria to antimicrobial drugs.

The invention also provides a vaccine composition comprising (i) a polypeptide, a polynucleotide or a vector of the invention together with (ii) a pharmaceutically acceptable carrier or diluent.

The invention also provides a plasmid containing a polynucleotide sequence of the invention under the control of a promoter.

The invention also provides a nucleic acid vaccine comprising (i) a plasmid of the invention; and (ii) a pharmaceutically acceptable carrier or diluent. Preferred nucleic acid vaccines which further comprise a transfection agent.

The invention also provides a vaccine comprising (i) a polypeptide of the invention optionally linked to a hapten molecule, and (ii) a pharmaceutically acceptable carrier or diluent.

The invention also provides a non-pathogenic microorganism or a cell from a human or animal species prone to infection by mpa-containing mycobacteria comprising a component on its surface which has been modified by a polypeptide of the invention.

The invention also provides a non-pathogenic microorganism or a cell from a human or animal species prone to infection by mpa-containing mycobacteria which has been transformed or transfected with a nucleic acid construct comprising a polynucleotide or plasmid of the invention, preferably the nucleic acid construct further comprises a polynucleotide which encodes the polypeptides of the GS region of MAP. Most preferably the gene or genes present in the nucleic acid construct are expressed.

The invention also provides a vaccine comprising (i) a non-pathogenic microorganism or a cell from a human or animal of the invention and (ii) a pharmaceutically acceptable carrier or diluent.

The invention also provides a non-pathogenic microorganism or a cell from a human or animal species prone to infection by mpa-containing mycobacteria comprising on its surface an antigenic determinant capable of being produced by the action of a polypeptide of the invention and which is capable of eliciting antibodies which bind the surface of MAP.

The invention also provides a normally pathogenic mycobacterium or pathogenic isolate thereof, whose pathogenicity is mediated in all or in part by the presence or expression of a polypeptide of the invention, which mycobacterium or isolate harbours an attenuating mutation in the polynucleotide sequence of the invention.

The invention also provides a vaccine comprising the mycobacterium or isolate of the invention and a pharmaceutically acceptable carrier or diluent. Preferably the attenuating mutation in the mycobacterium or isolate comprised in the vaccine is mediated by the insertion of one or more nucleotides.

The invention also provides a polynucleotide insertion element selected from:

(a) a polynucleotide comprising the nucleotide sequence set out in SEQ ID Nos. 3 or 4;
(b) a polynucleotide comprising a nucleotide sequence capable of hybridising to a fragment of the nucleotide sequence set out in SEQ ID No. 3, the fragment having the nucleotide sequence of nucleotides 1856-2543 of SEQ ID No. 3;
(c) a polynucleotide comprising a nucleotide sequence capable of hybridising to a fragment of the nucleotide sequence set out in SEQ ID No. 4, the fragment having the nucleotide sequence of nucleotides 1-688 of SEQ ID No. 4;
(d) a polynucleotide comprising a polynucleotide sequence which is degenerate as a result of the genetic code to the polynucleotide of SEQ ID No. 4 or a polynucleotide of (b);
(e) a polynucleotide having at least 75% homology to the nucleotide sequence of SEQ ID No. 3; and
(f) a polynucleotide having at least 75% homology to the nucleotide sequence of SEQ ID No. 4.

The invention provides as a preferred embodiment a vaccine comprising a mycobacterium or isolate of the invention wherein the attenuating mutation is mediated by insertion of a polynucleotide insertion element of the invention.

The invention also provides a polynucleotide probe or primer which comprises a fragment of at least 15 nucleotides of an insertion element of the invention, optionally carrying a revealing label.

The invention also provides a polypeptide in substantially isolated form which is encoded by an insertion element polynucleotide of the invention.

The invention also provides a polypeptide comprising at least 8 amino acids which is an immunogenic fragment of an insertion element polypeptide of the invention and which comprises an istA epitope.

The invention also provides a vector comprising an insertion element polynucleotide of the invention.

The invention also provides an expression vector comprising an insertion element polynucleotide of the invention, operably liked to regulatory sequences capable of directing expression of said polynucleotide in a host cell.

The invention also provides a method for preparing a mycobacterium or pathogenic isolate of the invention which method comprises transfecting animal or human isolate of an mpa containing pathogenic bacterium with a polynucleotide construct comprising an insertion element polynucleotide of the invention. In preferred embodiments transfection is effected by electroporation. In most preferred embodiments the polynucleotide comprised in the construct has the nucleotide sequence set out in SEQ ID No. 3 or 4.

BRIEF DESCRIPTION OF THE DRAWING

FIG. 1 shows the functional characterization of mpa.

DETAILED DESCRIPTION OF THE INVENTION

A. Polynucleotides.

Polynucleotides of the invention may comprise DNA or RNA. They may be single or double stranded. They may also be polynucleotides which include within them synthetic or modified nucleotides. Polynucleotides of the invention include polynucleotides in substantially isolated and isolated form. A number of different types of modification to oligonucleotides are known in the art. These include methylphosphonate and phosphorothioate backbones, addition of acridine or polylysine chains at the 3' and/or 5' ends of the molecule. For the purposes of the present invention, it is to be understood that the polynucleotides described herein may be modified by any method available in the art.

Such modifications may be carried out in order to enhance the in vivo activity or life span of polynucleotides of the invention.

Polynucleotides of the invention include:
i. a polynucleotide comprising the nucleotide sequence set out in SEQ ID No. 1 or the complement thereof;
ii. a polynucleotide comprising a polynucleotide sequence capable of hybridising to a polynucleotide having the sequence set out in SEQ ID No. 1 or a fragment thereof, preferred fragments having the sequence set out in nucleotides 110-1335 preferably 210-1335 of SEQ ID No. 1;
iii. a polynucleotide comprising a nucleotide sequence capable of hybridising to the complement of a polynucleotide having the sequence set out in SEQ ID No. 1 or a fragment thereof, preferred fragments having the nucleotide sequence set out in nucleotides 110-1335 preferably 210-1335 of SEQ ID No. 1;
iv. a polynucleotide comprising a polynucleotide sequence which is degenerate as a result of the genetic code to the nucleotide of SEQ ID No. 1 or a polynucleotide of (iii);
v. a polynucleotide having at least 80% homology to the nucleotide sequence of SEQ ID No. 1 or its complement;
vi. a polynucleotide comprising a nucleotide sequence set out in SEQ ID No. 3 or the complement thereof (SEQ ID No. 4);
vii. a polynucleotide comprising a nucleotide sequence capable of hybridising to a fragment of a polynucleotide having the sequence set out in SEQ ID No. 3, the fragment having the nucleotide sequence set out in nucleotides 1856-2543 of SEQ ID No. 3;
viii. a polynucleotide comprising a nucleotide sequence capable of hybridising to a fragment of a polynucleotide having the sequence set out in SEQ ID No. 4, the fragment having the nucleotide sequence of nucleotides 1-688 of SEQ ID No. 4;
ix. a polynucleotide comprising a polynucleotide sequence which is degenerate as a result of the genetic code to the polynucleotide of SEQ ID No. 4 or the polynucleotide of (vii);
x. a polynucleotide having at least 75% homology to the nucleotide sequence of SEQ ID No. 3; and
xi. a polynucleotide having at least 75% homology to the nucleotide sequence of SEQ ID No. 4.

Polynucleotides of the invention which are described as capable of hybridising to all or part of the DNA of SEQ ID No. 1 or the complements thereof or fragments of SEQ ID Nos. 3 and 4 will be generally at least 70%, preferably at least 75%, 80% or 90% or more preferably at least 95% homologous to the DNA to which they are described as hybridising over a region of at least 20, preferably at least 25 or 30 for instance at least 40, 60 or 100 or more contiguous nucleotides.

It is to be understood that skilled persons may, using routine techniques, make nucleotide substitutions that do not affect the polypeptide sequence encoded by the polynucleotides of the invention to reflect the codon usage of any particular host organism in which the polypeptides of the invention are to be expressed.

Any combination of the above mentioned degrees of homology and minimum sizes may be used to define polynucleotides of the invention, with the more stringent combinations (i.e. higher homology over longer lengths) being preferred. Thus for example a polynucleotide which is at least 80% homologous over 25, preferably 30 nucleotides forms one aspect of the invention, as does a polynucleotide which is at least 90% homologous over 40 nucleotides.

The homologues typically hybridise with the relevant polynucleotide at a level significantly above background. The signal level generated by the interaction between the homologue and the polynucleotide is typically at least 10 fold, preferably at least 100 fold, as intense as 'background' hybridisation. The intensity of interaction may be measured, for example, by radiolabelling the probe, e.g. with $^{32}$P. Selective hybridisation is typically achieved using conditions of medium to high stringency (for example 0.03M sodium chloride and 0.03M sodium citrate at from about 50° C. to about 60° C.). Methods of measuring polynucleotide homology are well known in the art. For example, the BLAST/N, BLAST/P and BLAST/X algorithms, for example used on their default settings, can be used to line up the sequences (as described in Altschul S. F. (1993) J Mol Evol 36:290-300; Altschul, S, F et al (1990) J Mol Biol 215:403-10) and to calculate the polynucleotide homologies discussed herein. These algorithms can also be used to calculate the polypeptide homologies referred to below.

The homologue may differ from a sequence in the relevant polynucleotide by at least 1, 2, 5, 10 or more substitutions, deletions or insertions over a region of over 25, preferably 30 nucleotides, for instance at least 40, 60 or 100 or more contiguous nucleotides of the homologue. Thus the homologue and polynucleotide may differ by 1, 2, 5, 10, 30 or more substitutions, deletions or insertions.

Polynucleotides of the invention may be in a substantially isolated form. It will be understood that the polynucleotide may be mixed with carriers or diluents which will not interfere with the intended purpose of the polynucleotide and still be regarded as substantially isolated. A polynucleotide of the invention may also be in a substantially purified form, in which case it will generally comprise the polynucleotide in a preparation in which more than 90%, e.g. 95%, 98% or 99% of the polynucleotide in the preparation is a polynucleotide of the invention.

Polynucleotides of the invention may be used to produce a primer, e.g. a PCR primer, a primer for an alternative amplification reaction, a probe e.g. labelled with a revealing label by conventional means using radioactive or non-radioactive labels, or the polynucleotides may be cloned into vectors. Such primers, probes and other fragments, such as fragments of the polynucleotides mentioned herein, will be at least 15, preferably at least 20, for example at least 25, 30 or 40 nucleotides in length, and are also encompassed by the term polynucleotides of the invention.

Polynucleotides such as a DNA polynucleotide and primers according to the invention may be produced recombinantly, synthetically, or by any means available to those of skill in the art. They may also be cloned by standard techniques.

In general, primers will be produced by synthetic means, involving a step wise manufacture of the desired nucleic acid sequence one nucleotide at a time. Techniques for accomplishing this using automated techniques are readily available in the art.

Longer polynucleotides will generally be produced using recombinant means, for example using a PCR (polymerase chain reaction) cloning techniques. This will involve making a pair of primers (e.g. of about 15-30 nucleotides) to a region of the mpa gene which it is desired to clone, bringing the primers into contact with mRNA or cDNA, performing a polymerase chain reaction under conditions which bring about amplification of the desired region, isolating the amplified fragment (e.g. by purifying the reaction mixture on an agarose gel) and recovering the amplified DNA. The primers may be designed to contain suitable restriction enzyme recognition sites so that the amplified DNA can be cloned into a suitable cloning vector. Although in general the techniques mentioned herein are well known in the art, reference may be made in particular to Sambrook et al., Molecular Cloning, A Laboratory Manual (1989) and Ausubel et al., Current Protocols in Molecular Biology (1995), John Wiley & Sons, Inc.

Polynucleotides which are not 100% homologous to the sequences of the present invention but fall within the scope of the invention can be obtained in a number of ways. Other isolates or strains of pathogenic mycobacteria will be expected to contain allelic variants of the mpa sequence described herein may be obtained for example by probing genomic DNA libraries made from such pathogenic mycobacteria. In addition, other mycobacterial homologues of mpa in pathogenic M. avium such as M. avium strain 104 may be obtained and such homologues and fragments thereof in general will be capable of selectively hybridising to SEQ ID No. 1. Such sequences may be obtained by probing cDNA libraries made from or genomic DNA libraries from other mycobacterial species and their isolates, and probing such libraries with probes comprising all or part of SEQ ID. No. 1 as defined above under conditions of medium to high stringency (for example 0.03M sodium chloride and 0.03M sodium citrate at from about 50° C. to about 60° C.). Homologues of the mpa gene in other pathogenic M. avium may also be obtained by polymerase chain reaction or other method of amplifying these mpa genes using primers derived from SEQ ID No. 1 or the complement thereof.

The invention includes allelic variants and species homologues which may also for example be obtained using degenerate PCR which will use primers designed to target sequences within the variants and homologues encoding conserved amino acid sequences. The primers will contain one or more degenerate positions and will be used at stringency conditions lower than those used for cloning sequences with single sequence primers against known sequences.

Alternatively, such polynucleotides may be obtained by site directed mutagenesis of the mpa sequence or allelic variants thereof. This may be useful where for example any silent codon changes are required to sequences in order to optimise codon preferences for a particular host cell in which the polynucleotide sequences are being expressed. Other sequence changes may be desired in order to introduce restriction enzyme recognition sites, or to alter the property or function of the polypeptides encoded by the polynucleotides.

Such altered property or function will include the addition of amino acid sequences of consensus signal peptides known in the art to effect transport and secretion of the modified polypeptide of the invention. Another altered property will include mutagenesis of a catalytic residue or generation of fusion proteins with another polypeptide. Such fusion proteins may be with an enzyme, with an antibody or with a cytokine or other ligand for a receptor, to target a polypeptide of the invention to a specific cell type in vitro or in vivo or to enhance immune recognition and reactivity.

The invention further provides double stranded polynucleotides comprising a polynucleotide of the invention and its complement.

Polynucleotides or primers of the invention may carry a revealing label. Suitable labels include radioisotopes such as $^{32}P$ or $^{35}S$, enzyme labels, or other protein labels such as biotin. Such labels may be added to polynucleotides or primers of the invention and may be detected using by techniques known per se.

Polynucleotides or primers of the invention or fragments thereof labelled or unlabelled may be used by a person skilled in the art in nucleic acid-based tests for detecting or sequencing mpa and its homologues in samples of body fluids, tissues or excreta from animals and humans and to food and environmental samples e.g. water. Human and animal body fluids include sputum, blood, serum, plasma, saliva, milk, urine, csf, semen, faeces and infected discharges. Tissues include intestine, mouth ulcers, skin, lymph nodes, spleen, lung and liver obtained surgically or by a biopsy technique. Animals particularly include commercial livestock such as cattle, sheep, goats, deer, rabbits but wild animals and animals in zoos may also be tested.

Such tests for detecting generally comprise bringing a biological sample containing DNA or RNA into contact with a probe comprising a polynucleotide or primer of the invention under hybridising conditions and detecting any duplex formed between the probe and nucleic acid in the sample. Such detection may be achieved using techniques such as PCR or by immobilising the probe on a solid support, removing nucleic acid in the sample which is not hybridised to the probe, and then detecting nucleic acid which has hybridised to the probe. Alternatively, the sample nucleic acid may be immobilised on a solid support, and the amount of probe bound to such a support can be detected. Suitable assay methods of this any other formats can be found in for example WO89/03891 and WO90/13667.

Methods for sequencing mpa or IS1612 and their homologues include bringing a biological sample containing target DNA or RNA into contact with a probe comprising a polynucleotide or primer of the invention under hybridising conditions and determining the sequence by, for example the Sanger dideoxy chain termination method (see Sambrook et al.). Such a method generally comprises elongating, in the presence of suitable reagents, the primer by synthesis of a strand are to the target DNA or RNA and selectively terminating the elongation reaction at one or more of an A, C, G or T/U residue: allowing strand elongation and termination reaction to occur; separating out according to size the elongated products to determine the sequence of the nucleotides at which selective termination has occurred. Suitable reagents include a DNA polymerase enzyme, the deoxynucleotides dATP, dCTP, dGTP and dTTP, a buffer and ATP. Dideoxynucleotides are used for selective termination.

Polynucleotides of the invention or fragments thereof labelled or unlabelled may also be used to identify and characterise different strains of MAP, and other mpa-containing pathogenic mycobacteria and properties such as drug resistance or susceptibility. The probes of the invention may conveniently be packaged in the form of a test kit in a suitable container for storage and transport. In such kits the probe may be bound to a solid support where the assay format for which the kit is designed requires such binding. The kit may also contain suitable reagents for treating the sample to be probed, hybridising the probe to nucleic acid in the sample, control reagents, instructions, and the like. The kit also preferably involves methods known in the art such as PCR or LCR.

The use of polynucleotides of the invention in the diagnosis of inflammatory diseases such as Crohn's disease or sarcoidosis in humans or Johne's disease in animals form preferred aspects of the invention. The polynucleotides may also be used in the prognosis of these diseases. For example, the response of a human or animal subject in response to antibiotic, vaccination or other therapies may be monitored by utilising the diagnostic methods of the invention over the course of a period of treatment and following such treatment.

The invention provides probes capable of detecting the presence of polynucleotides of the invention (which can for example be used in the detection or diagnostic methods mentioned herein). Typically such probes are polynucleotide.

However, such probes can be non-polynucleotides, such as proteins (for example protein polynucleotides).

The use of mpa polynucleotides (particularly in the form of probes and primers) of the invention in the above-described methods form a further aspect of the invention, particularly for the detection, diagnosis or prognosis of MAP infections.

The present invention also provides polynucleotides encoding the polypeptides of the invention described below. Because such polynucleotides will be useful as sequences for recombinant production of polypeptides of the invention, it is not necessary for them to be selectively hybridisable to the sequence of SEQ ID No. 1 although this will generally be desirable. Otherwise, such polynucleotides may be labelled, used, and made as described above if desired. Preferably the polynucleotides of the invention encode polypeptides which possess mpa activity. Mpa polypeptides of the invention are described below.

The present invention also provides the polynucleotide sequence of an IS21-like insertion element hereafter termed IS1612 and related polynucleotide sequences as described in items vi-xi and relevant passages above (hereafter referred to as the IS1612 polynucleotides of the invention). The invention in this aspect also provides a polynucleotide construct comprising the IS1612 polynucleotides of the invention which construct is in a suitable form for transfection into mpa-containing bacterial cells, preferably mpa-containing mycobacterial cells originating from an animal or human. The invention further provides a method for attenuating a normally pathogenic mycobacterium whose pathogenicity is mediated in all or in part by the presence or expression of the mpa polynucleotides (i-v and relevant passages above) of the invention, which method comprises transfecting into a mycobacterial cell or isolate of said pathogenic mycobacterium a polynucleotide construct comprising the IS1612 polynucleotides of the invention.

Transfection can be carried out by electroporation or any other method known in the art such that the function of the mpa gene is knocked out, resulting in a mutated attenuated form of these normally pathogenic mycobacteria.

The IS1612 element encodes from SEQ ID No. 4 two polypeptides the first of which in its entirety is new and forms part of the present invention. The entire amino acid sequence of the first polypeptide, termed istA, is encoded by nucleotides 98-1678 of SEQ ID No. 4 and is given as SEQ ID No. 5. The IS1612 polypeptides from the invention are further described below.

B. Polypeptides.

Polypeptides of the invention include polypeptides in substantially isolated form which comprise the sequence set out in SEQ ID No. 2 or SEQ ID No. 5. Polypeptides further include variants of such sequences, including naturally occurring variants and synthetic variants which are substantially homologous to said polypeptides. In this context, substantial homology is regarded as a sequence which has at least 70%, e.g. 80%, 90%, 95% or 98% amino acid homology (identity) over 30 amino acids with the sequence of SEQ ID No. 2.

Polypeptides of the invention also include fragments of the above mentioned full length polypeptides and variants thereof, including in particular any fragments of the sequence set out in SEQ ID No. 2 and the fragment having the sequence of amino acids 1-211 as set out in SEQ ID No. 5. Preferred fragments such as residues 158-211 and 380-444 of SEQ ID No 2, include those which include an epitope and especially in the use of related polypeptides to SEQ ID No. 2 an epitope which is specific to the pathogenicity of the mycobacterial cell from which the polypeptide is derived. Suitable fragments will be at least 8, e.g. 10, 12, 15 or 20 amino acids in size. Polypeptide fragments of mpa and allelic and species variants thereof may contain one or more (e.g. 2, 3, 5, or 10) substitutions, deletions or insertions, including conserved substitutions, or modifications of amino acids such as phosphorylation of serine or threonine.

Conserved substitutions may be made according to the following table which indicates conservative substitutions, where amino acids on the same block in the second column and preferably in the same line in the third column may be substituted for each other:

| | | |
|---|---|---|
| ALIPHATIC | Non-polar | G A P |
| | | I L V |
| | Polar - uncharged | C S T M |
| | | N Q |
| | Polar - charged | D E |
| | | K R |
| AROMATIC | | H F W Y |
| OTHER | | N Q D E |

Epitopes may be T-cell epitopes or antibody epitopes determined, for example, by techniques such as peptide scanning techniques as described by Geysen et al, Mol. Immunol., 23, 709-715 (1986) as well as other techniques known in the art.

The term "an epitope which is specific to the pathogenicity of the mycobacterial cell" means that the epitope is encoded by a portion of the mpa gene, or by the corresponding ORF sequences in other mycobacteria which can be used to distinguish mycobacteria which are pathogenic from related non-pathogenic mycobacteria including non-pathogenic species of *M. avium*. This may be determined using routine methodology. A candidate epitope may be prepared and used to immunise an animal such as a rat or rabbit in order to generate antibodies. The antibodies may then be used to detect the presence of the epitope in pathogenic mycobacteria and to confirm that non-pathogenic mycobacteria do not contain any proteins which react with the epitope. Epitopes may be linear or conformational.

Polypeptides of the invention may be in a substantially isolated form. It will be understood that the polypeptide may be mixed with carriers or diluents which will not interfere with the intended purpose of the polypeptide and still be regarded as substantially isolated. A polypeptide of the invention may also be in a substantially purified form, in which case it will generally comprise the polypeptide in a preparation in which more than 90%, e.g. 95%, 98% or 99% of the polypeptide in the preparation is a polypeptide of the invention. Polypeptides of the invention may be modified for example by the addition of histidine residues to assist their purification or by the addition of a signal sequence to promote their secretion from a cell, or a transmembrane sequence to facilitate their immobilisation in a membrane or lipid bilayer.

Thus, polypeptides of the invention include in particular fusion proteins which comprise a polypeptide encoded all or part of the mpa gene fused at its N- or C-terminus to a second sequence to provide the desired property or function. Sequences which promote secretion from a cell include, for example the yeast a-factor signal sequence.

A polypeptide of the invention may be labelled with a revealing label. The revealing label may be any suitable label which allows the polypeptide to be detected. Suitable labels include radioisotopes e.g. $^{125}I$, enzymes, antibodies, polynucleotides and linkers such as biotin. Labelled polypeptides of the invention may be used in diagnostic procedures such as immunoassays in order to determine the amount of a polypeptide of the invention in a sample. Polypeptides or labelled polypeptides of the invention may also be used in serological or cell mediated immune assays for the detection of immune reactivity to said polypeptides in animals and humans using standard protocols.

A polypeptide or labelled polypeptide of the invention or fragment thereof may also be fixed to a solid phase, for example the surface of an immunoassay well or dipstick. Such labelled and/or immobilised polypeptides may be packaged into kits in a suitable container for transport and storage along with suitable reagents, controls, instructions and the like.

Such polypeptides and kits may be used in methods of detection of antibodies or cell mediated immunoreactivity, to the mycobacterial proteins and peptides encoded by the mpa gene and its allelic variants and fragments, using immunoassay. Such host antibodies or cell mediated immune reactivity will occur in humans or animals with an immune system which detects and reacts against polypeptides of the invention. The antibodies may be present in a biological sample from humans or animals. The biological sample may be a sample as defined above particularly blood, milk or saliva.

Immunoassay methods are well known in the art and will generally comprise:
(a) providing a polypeptide of the invention comprising an epitope bindable by an antibody against said mycobacterial polypeptide;
(b) incubating a biological sample with said polypeptide under conditions which allow for the formation of an antibody-antigen complex; and
(c) determining whether antibody-antigen complex comprising said polypeptide is formed.

Immunoassay methods for cell mediated immune reactivity in animals and humans are also well known in the art (e.g. as described by Weir et al 1994, J. Immunol Methods 176; 93-101) and will generally comprise:
(a) providing a polypeptide of the invention comprising an epitope bindable by a lymphocyte or macrophage or other cell receptor,
(b) incubating a cell sample with said polypeptide under conditions which allow for a cellular immune response such as release of cytokines or other mediator to occur, and
(c) detecting the presence of said cytokine or mediator in the incubate.

Polypeptides of the invention may be made by synthetic means (e.g. as described by Geysen et al., 1996) or recombinantly, as described below.

Preferred polypeptides of the invention include Sequence ID No. 2 and particularly residues 158-211 and 380-444 thereof, and amino acids 1-211 of Sequence ID No. 5. Fragments as defined above from these regions are particularly preferred. The polypeptides and fragments thereof may contain amino acid alterations as defined above.

Polypeptides of the invention or fragments thereof labelled or unlabelled may also be used to identify and characterise different strains of MAP, or other mpa-containing pathogenic mycobacteria and properties such as drug resistance or susceptibility.

The use of polypeptides of the invention in the diagnosis of inflammatory diseases such as Crohn's disease or sarcoidosis in humans or Johne's disease in animals form a preferred aspect of the invention. The polypeptides may also be used in the prognosis of these diseases. For example, the response of a human or animal subject to antibiotic or other therapies may be monitored by utilizing the diagnostic methods of the invention over the course of a period of treatment and following such treatment. The use of mpa polypeptides of the invention in the above-described methods form a further aspect of the invention, particularly for the detection, diagnosis or prognosis of mycobacterial preferably MAP infections.

Polypeptides of the invention may also be used in assay methods for identifying candidate chemical compounds which will be useful in inhibiting, binding to or disrupting the function of said polypeptides required for pathogenicity. In general, such assays involve bringing the polypeptide into contact with a candidate inhibitor compound and observing the ability of the compound to disrupt, bind to or interfere with the polypeptide. There are a number of ways in which the assay may be formatted. For example, those polypeptides which have an enzymatic function may be assayed using labelled substrates for the enzyme, and the amount of, or rate of, conversion of the substrate into a product measured, e.g. by chromatography such as HPLC or by a colourimetric assay. Suitable labels include $^{35}$S, $^{125}$I, biotin or enzymes such as horse radish peroxidase.

Candidate chemical compounds which may be used may be natural or synthetic chemical compounds used in drug screening programmes. Extracts of plants which contain several characterised or uncharacterised components may also be used.

Alternatively, a polypeptide of the invention may be screened against a panel of peptides, nucleic acids or other chemical functionalities which are generated by combinatorial chemistry. This will allow the definition of chemical entities which bind to polypeptides of the invention. Typically, the polypeptide of the invention will be brought into contact with a panel of compounds from a combinatorial library, with either the panel or the polypeptide being immobilized on a solid phase, under conditions suitable for the polypeptide to bind to the panel. The solid phase will then be washed under conditions in which only specific interactions between the polypeptide and individual members of the panel are retained, and those specific members may be utilised in further assays or used to design further panels of candidate compounds. Binding of polypeptides of the invention to specific ligands may be identified using an antibody to said polypeptide or a polypeptide bearing a revealing label.

For example, a number of assay methods to define peptide interaction with peptides are known. For example, WO86/00991 describes a method for determining mimotopes which comprises making panels of catamer preparations, for example octamers of amino acids, at which one or more of the positions is defined and the remaining positions are randomly made up of other amino acids, determining which catamer binds to a protein of interest and re-screening the protein of interest against a further panel based on the most reactive catamer in which one or more additional designated positions are systematically varied. This may be repeated throughout a number of cycles and used to build up a sequence of a binding candidate compound of interest.

WO89/03430 describes screening methods which permit the preparation of specific mimotopes which mimic the immunological activity of a desired analyte. These mimotopes are identified by reacting a panel of individual peptides wherein said peptides are of systematically varying hydrophobicity, amphipathic characteristics and charge patterns, using an antibody against an antigen of interest. Thus in the present case antibodies against a polypeptide of the invention may be employed and mimotope peptides from such panels may be identified. We particularly recognise that antibodies, including monoclonal antibodies, to GPL's from pathogenic MAP may be identified by their ability to bind to these organisms, but not to mutated forms in which the function of the mpa gene has been knocked-out. These antibodies may be used to screen phage-displayed peptide libraries for immunogenic mimics of GPL epitopes, and that such peptide immunogenic mimics may be used in the development of anti-GPL vaccines [Phalipon et al. Eur. J. Immunol. 27:2620-2625, 1997].

C. Vectors.

Polynucleotides of the invention can be incorporated into a recombinant replicable vector. The vector may be used to replicate the nucleic acid in a compatible host cell. Thus in a further embodiment, the invention provides a method of making polynucleotides of the invention by introducing a polynucleotide of the invention into a replicable vector, introducing the vector into a compatible host cell, and growing the host cell under conditions which bring about replication of the vector. The vector may be recovered from the host cell. Suitable host cells are described below in connection with expression vectors.

D. Expression Vectors.

Preferably, a polynucleotide of the invention in a vector is operably linked to a regulatory sequence which is capable of providing for the expression of the coding sequence by the host cell, i.e. the vector is an expression vector. The term "operably linked" refers to a juxtaposition wherein the components described are in a relationship permitting them to function in their intended manner. A regulatory sequence "operably linked" to a coding sequence is ligated in such a way that expression of the coding sequence is achieved under condition compatible with the control sequences.

The term "regulatory sequences" includes promoters and enhancers and other expression regulation signals. These may be selected to be compatible with the host cell for which the expression vector is designed. For example, yeast regulatory sequences include S. cerevisiae GAL4 and ADH promoters, S. pombe nmt1 and adh promoters. Mammalian promoters, such as β-actin promoters, may be used. Mammalian promoters also include the metallothionein promoter which can upregulate expression in response to heavy metals such as cadmium and is thus an inducible promoter. Tissue-specific promoters, for example neuronal cell specific may be used. Viral promoters may also be used, for example the Moloney murine leukaemia virus long terminal repeat (MMLV LTR), the promoter roes sarcoma virus (RSV) LTR promoter, the SV40 promoter, the human cytomegalovirus (CMV) IE promoter, herpes simplex virus promoters or adenovirus promoters. All these promoters are readily available in the art.

Such vectors may be transformed into a suitable host cell as described above to provide for expression of a polypeptide of the invention. Thus, in a further aspect the invention provides a process for preparing polypeptides according to the invention which comprises cultivating a host cell transformed or transfected with an expression vector as described above under conditions to provide for expression by the vector of a coding sequence encoding the polypeptides, and recovering the expressed polypeptides.

The vectors may be for example, plasmid, virus or phage vectors provided with an origin of replication, optionally a promoter for the expression of the said polynucleotide and optionally a regulator of the promoter. The vectors may contain one or more selectable marker genes, for example an ampicillin resistance gene in the case of a bacterial plasmid or a neomycin resistance gene for a mammalian vector. Vectors may be used in vitro, for example for the production of RNA or used to transfect or transform a host cell. The vector may also be adapted to be used in vivo, for example in a method of gene therapy or a DNA vaccine.

The use of mammalian host cells is expected to provide for such post-translational modifications (e.g. myristolation, glycosylation, truncation, lapidation and tyrosine, serine or threonine phosphorylation) as may be needed to confer optimal biological activity on recombinant expression products of the invention. Such cell culture systems in which polypeptide of the invention are expressed may be used in assay systems to identify candidate substances which interfere with or enhance the functions of the polypeptides of the invention in the cell.

A further embodiment of the invention provides host cells transformed or transfected with the vectors for the replication and expression of polynucleotides of the invention. The cells will be chosen to be compatible with the said vector and may for example be bacterial, yeast, insect or mammalian.

Polynucleotides according to the invention may also be inserted into the vectors described above in an antisense orientation in order to provide for the production of antisense RNA. Antisense RNA or other antisense polynucleotides may also be produced by synthetic means. Such antisense polynucleotides may be used in a method of controlling the levels of mpa or its variants or species homologues.

E. Antibodies.

The invention also provides monoclonal or polyclonal antibodies to polypeptides of the invention or fragments thereof. Preferred fragments include amino acid residues 158-211 and 380-444 of SEQ ID No. 2. The invention further provides a process for the production of monoclonal or polyclonal antibodies to polypeptides of the invention. Monoclonal antibodies may be prepared by conventional hybridoma technology using the polypeptides of the invention or peptide fragments thereof, as immunogens. Polyclonal antibodies may also be prepared by conventional means which comprise inoculating a host animal, for example a rat or a rabbit, with a polypeptide of the invention or peptide fragment thereof and recovering immune serum. In order that such antibodies may be made, the invention also provides polypeptides of the invention or fragments thereof haptenised to another polypeptide for use as immunogens in animals or humans or admixed with adjuvants. For the purposes of this invention, the term "antibody", unless specified to the contrary, includes fragments of whole antibodies which retain their binding activity for a tumour target antigen. Such fragments include Fv, F(ab') and F(ab'), fragments, as well as single chain antibodies. Furthermore, the antibodies and fragments thereof may be humanised antibodies, e.g. as described in EP-A-239400.

Antibodies may be used in method of detecting polypeptides of the invention present in biological samples by a method which comprises:
(a) providing an antibody of the invention;
(b) incubating a biological sample with said antibody under conditions which allow for the formation of an antibody-antigen complex; and
(c) determining whether antibody-antigen complex comprising said antibody is formed.

Antibodies of the invention may be used to detect MAP in a sample, such as a tissue sample or milk, using standard immunohistochemical techniques, which method comprises:
(a) providing an antibody of the invention;
(b) treating the tissue section or other sample with lysozyme or process to access the epitope;
(c) incubating the tissue section or other sample with said antibody under conditions which allow the formation of an antibody-antigen complex; and
(d) revealing the presence of bound antibody by any one of the standard histochemical methods known in the art.

Antibodies of the invention may be bound to a solid support and/or packaged into kits in a suitable container for storage and transport along with suitable reagents, controls, instructions and the like. Antibodies of the invention may be used in the detection, diagnosis and prognosis of diseases as discussed above in relation to polypeptides of the invention.

F. Compositions.

The present invention also provides compositions comprising a polynucleotide or polypeptide of the invention together with a carrier or diluent. Compositions of the invention also include compositions comprising a nucleic acid, particularly and expression vector, of the invention. Compositions further include those carrying a recombinant virus of the invention. Such compositions include pharmaceutical compositions in which case the carrier or diluent will be pharmaceutically acceptable.

Pharmaceutically acceptable carriers or diluents include those used in formulations suitable for inhalation as well as oral, parenteral (e.g. intramuscular or intravenous or transcutaneous) administration. The formulations may conveniently be presented in unit dosage form and may be prepared by any of the methods well known in the art of pharmacy. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both.

For example, formulations suitable for parenteral administration include aqueous and non-aqueous sterile injection solutions which may contain anti-oxidants, buffers, bacteriostatics and solutes which render the formulation isotonic with the blood of the intended recipient, and aqueous and non-aqueous sterile suspensions which may include suspending agents and thickening agents, and liposomes or other microparticulate systems such as gold particles for use in the DNA gun, all of which are designed to target the polynucleotide or the polypeptide of the invention to blood components or one or more organs, or to target cells such as skin cells, dendritic cells, muscle cells, or mucosal M cells of the intestine after oral administration or rectal administration or of the nasal and respiratory mucosa.

G. Vaccines.

In another aspect, the invention provides novel vaccines for the prevention and treatment of infections caused by MAP and other mpa-containing pathogenic mycobacteria in animals and humans. The term "vaccine" as used herein means an agent used to stimulate the immune system of a vertebrate, particularly a warm blooded vertebrate including humans, so as to provide protection against future harm by an organism to which the vaccine is directed or to assist in the eradication of an organism in the treatment of established infection. The immune system will be stimulated by the production of cellular immunity and antibodies, desirably neutralizing antibodies, directed to epitopes found on or in a pathogenic mycobacterium which expresses the mpa gene of the invention. The antibody so produced may be any of the immunological classes, such as the immunoglobulins A, D, E, G or M. Vaccines which stimulate the production of IgA are interest since this is the principle immunoglobulin produced by the secretory system of warm-blooded animals, and the production of such antibodies will help prevent infection or colonization of the intestinal tract. However an IgM and IgG response will also be desirable for vaccination against systemic infections such as Crohn's disease or Johne's disease.

Vaccines of the invention include naked nucleic acid vaccines such as DNA vaccines. Naked nucleic acid vaccines of the invention include polynucleotides of the invention or fragments thereof in suitable vectors which may be administered as naked nucleic acid using standard protocols. The preferred nucleic acid vaccines of the invention are DNA vaccines which comprise at least one DNA polynucleotide of the invention incorporated into a plasmid under the control of a strong promoter. Suitable strong promoters are viral promoters such as the Muloney murine leukaemia virus long-terminal repeat (MMLV LTR), the promoter rouse sarcoma virus (RSV) LTR promoter, the SV40 promoter, the human cytomegalovirus (CMV) IE promoter, herpes simplex virus promoters or adenovirus promoters. The preferred promoter is CMV. The nucleic acid vaccines of the invention made be administered intradermally, subcutaneously, intramuscularly or mucosally by inhalation, ingestion or intra-rectal installation. The nucleic acid vaccine of the invention may be incorporated into a suitable formulation, absorbed or coated onto particles which are appropriate for ingestion into macrophages or antigen presenting cells. Such particles may include gold particles and may be administered by using a gene gun. The nucleic acid vaccine of the invention may also be carried within another organism such as disabled *salmonella, M. Bovis* BCG, *M. Smegmatis* or other mycobacteria, Corynebacteria, or other agents according to established protocol.

Immunising formulations may advantageously include an adjuvant.

When the polynucleotide of the invention is administered as a nucleic acid vaccine, the amount of nucleic acid administered is typically in the range of from 50-500 µg. Uptake of the nucleic acid vaccines of the invention by mammalian cells may be enhanced by several transfection techniques, for example, those including the use of transfection agents. Examples of these agents include catonication (for example calcium phosphate and DEAE-dextran) and lipofectants (for example Lipofectam™ and Transfectam™). Confirmation of successful expression of mpa in a bacterium can be achieved by analysing surface sugars for acetylation using high pressure liquid chromatography and other methods known in the art. Typically, the nucleic acid in the vaccine is mixed with the transfection agent to produce a composition. Preferably the nucleic acid vaccine with or without transfection agent is combined with a pharmaceutically acceptable carrier or diluent to produce a pharmaceutical composition. Suitable carriers and diluents include isotonic saline solution, for example, phosphate buffered saline. The route of administration and dosages described are intended only a guide since the skilled practitioner will be able to readily determine the optimum route of administration and dosage for any particular patient and condition.

In addition to the above it is also possible to prepare "live" vaccines containing non-pathogenic microorganisms which express or are capable of causing to be expressed one or more polypeptides of the invention. Non-pathogenic microorganisms may be naturally non-pathogenic microorganisms or attenuated microorganisms which are normally pathogenic. Suitable attenuated microorganisms are known in the art and include attenuated bacteria such as attenuated *salmonella* and attenuated viruses such as vaccinia virus. Transformation of the mpa gene or other polynucleotides of the invention into the attenuated microorganism is preferably completed in vitro. It is also within the invention to transfect cells of a human or animal to be vaccinated with a polynucleotide of the invention in vitro although it is preferred that transfection of a host cell should occur in vivo by, for example, DNA vaccination as described above.

It shall also be appreciated that the invention provides a non-pathogenic microorganism or human or animal cell which has on its surface a cell surface component produced by modification of a cell surface substrate with a polypeptide of the invention. Preferably, the polypeptide of the invention is expressed within the non-pathogenic microorganism or human or animal cell upon which the modified cell surface component resides. Thus the invention provides a non-pathogenic microorganism or human or animal cell which has been transformed or transfected with a polynucleotide of the invention which is expressed and results in the presence of the modified cell surface component. It should also be appreciated that it is within this invention to treat the surface of cells exhibiting the cell surface substrate with preformed polypeptide of the invention to produce cells having the modified cell surface component. It is also within this invention to provide a non-pathogenic microorganism or human or animal cell wherein an identical antigenic determinant to the modified cell surface component is produced on a cell surface using polypeptides other than mpa which fulfil an identical role to mpa.

In a further aspect vaccines of the invention which function by expressing mpa including, for example, nucleic acid vaccines or live vaccines mentioned above, may be augmented by expressing all of the polypeptides encoded for in the ORFs of the GS region identified in MAP along with mpa of the invention. The polypeptides encoded for by the ORFs of GS in MAP and the polynucleotide sequence of GS in MAP were disclosed and characterised in PCT/GB96/03221. These vaccines may be obtained by transforming the attenuated microorganism mentioned above with a polynucleotide of the invention which comprises the mpa gene or previously defined related sequence thereof together with the genes encoding the polypeptides associated with the GS region in MAP. For the naked nucleic acid vaccines transfection of a host cell in vivo may be achieved by nucleic acid vaccination using the mpa gene or the previously defined related sequence thereof together with the genes encoding the polypeptides associated with the GS element of MAP under the control of one or more suitable promoters.

Polypeptides of the invention or fragments thereof in substantially isolated form may also be used as vaccines by injection, inhalation, oral administration or by transcutaneous application according to standard protocols. Adjuvants (such as Iscoms or polylactide-coglycolide encapsulation), cytokines such as IL-12 and other immunomodulators may be used for the selective enhancement of the cell mediated or humeral immunological responses. Vaccination with polynucleotides and/or polypeptides of the invention may be undertaken to increase the susceptibility of pathogenic mycobacteria to antimicrobial agents in vivo.

In instances wherein the polypeptide is correctly configured so as to provide the correct epitope, but is too small to be immunogenic, the polypeptide may be linked to a suitable carrier.

A number of techniques for obtaining such linkage are known in the art, including the formation of disulphide linkages using N-succinimidyl-3-(2-pyridylthio)propionate (SPDP) and succinimidyl 4-(N-maleimido-methyl)cyclohexane-1-carboxylate (SMCC) obtained from Pierce Company, Rockford, Ill., (if the peptide lacks a sulfhydryl group, this can be provided by addition of a cysteine residue). These reagents create a disulphide linkage between themselves and peptide cysteine residues on one protein and an amide linkage through the epsilon-amino on a lysine, or other free amino group in the other. A variety of such disulphide/amide-forming agents are known. See, for example, Immun. Rev. (1982) 62:185. Other bifunctional coupling agents form a thioether rather than a disulphide linkage. Many of these thio-ether-forming agents are commercially available and include reactive esters of 6-maleimidocaproic acid, 2-bromoacetic acid, 2-iodoacetic acid, 4-(N-maleimido-methyl)cyclohexane-1-carboxylic acid, and the like. The carboxyl group can be activated by combining them with succinimide or 1-hydroxyl-2-nitro-4-sulfonic acid, sodium salt. Additional methods of coupling antigens employs the rotavirus/"binding peptide" system described in EP 259,149, the disclosure of which is incorporated herein by reference. The foregoing list is not meant to be exhaustive, and modifications of the named compounds can clearly be used.

Any carrier may be used which does not itself induce the production of antibodies harmful to the host. Suitable carriers are typically large, slowly metabolized macromolecules such as proteins; polysaccharides, such as latex functionalized Sepharose 7, agarose, cellulose, cellulose beads and the like; polymeric amino acids, such as polyglutamic acid and polylysine, and the like; amino acid copolymers; and inactive virus particles. Especially useful protein carriers are serum albumens, keyhole limpet hemocyanin, immunoglobulin molecules, thyroglobulin, ovalbumin, tetanus toxoid, and other proteins well known to those skilled in the art. Particularly useful also are controlled release microspheres composed of polylactide coglycolide typically 75:25 and typically 50 μM in diameter.

Polynucleotide and polypeptide vaccines of the invention adsorbed onto such microspheres may be zinc stabilised. Lamella polymers of chitin or chitosan in microparticulate form typically 100 nM may also be employed.

The immunogenicity of the epitopes may also be enhanced by preparing them in mammalian or yeast systems fused with or assembled with particle-forming proteins such as, for example, that associated with hepatitis B surface antigen. See, e.g., U.S. Pat. No. 4,722,840. Constructs wherein the epitope is linked directly to the particle-forming protein coding sequences produce hybrids which are immunogenic with respect to the epitope. In addition, all of the vectors prepared include epitopes specific to HBV, having various degrees of immunogenicity, such as, for example, the pre-S peptide.

In addition, portions of the particle-forming protein coding sequence may be replaced with codons encoding an epitope of the invention. In this replacement, regions which are not required to mediate the aggregation of the units to form immunogenic particles in yeast or mammals can be deleted, thus eliminating additional HBV antigenic sites from competition with the epitope of the invention.

Vaccines may be prepared from one or more immunogenic polypeptides of the invention.

The polypeptides for use in vaccines may be expressed in various host cells (e.g., bacteria, yeast, insect, or mammalian cells), or alternatively may be isolated from viral preparations or made synthetically.

The preparation of vaccines which contain an immunogenic polypeptide(s) as active ingredients, is known to one skilled in the art. Typically, such vaccines are prepared as injectables, or as suitably encapsulated oral preparations and either liquid solutions or suspensions; solid forms suitable for solution in, or suspension in, liquid prior to ingestion or injection may also be prepared. The preparation may also be emulsified, or the protein encapsulated in liposomes. The active immunogenic ingredients are often mixed with excipients which are pharmaceutically acceptable and compatible with the active ingredient. Suitable excipients are, for example, water, saline, dextrose, glycerol, ethanol, or the like and combinations thereof. In addition, if desired, the vaccine may contain minor amounts of auxiliary substances such as wetting or emulsifying agents, pH buffering agents, and/or adjuvants which enhance the effectiveness of the vaccine. Examples of adjuvants which may be effective include but are not limited to: aluminum hydroxide, N-acetyl-muramyl-L-threonyl-D-isoglutamine (thr-MDP), N-acetyl-nor-muramyl-L-alanyl-D-isoglutamine (CGP 11637, referred to as nor-MDP), N-acetylmuramyl-L-alanyl-D-isoglutaminyl-L-alanine-2-(1'-2'-dipalmitoyl-sn-glycero-3-hydroxyphosphoryloxy)-ethylamine (CGP 19835A, referred to as MTP-PE), and RIBI, which contains three components extracted from bacteria, monophosphoryl lipid A, trehalose dimycolate and cell wall skeleton (MPL+TDM+CWS) in a 2% squalene/Tween 7 80 emulsion. Adjuvants may also include MF59 or sub-units of Cholera toxin which may be mutated or fragments thereof, or DNA itself which is an adjuvant known in the art. The effectiveness of an adjuvant may be determined by measuring the amount of antibodies directed against an immunogenic polypeptide containing an antigenic sequence resulting from administration of this polypeptide in vaccines which are also comprised of the various adjuvants.

In a further aspect of the invention there is provided an attenuated vaccine comprising a normally pathogenic mycobacteria which harbours an attenuating mutation in the mpa gene or one or more of its homologues.

The mycobacteria may be used in the form of a killed bacteria or as a live attenuated vaccine. There are advantages to using a live attenuated vaccine. If the whole live organism is used rather than dead cells or selected cell components which may exhibit modified or denatured antigens, protein antigens in the outer membrane will tend to maintain their tertiary and quaternary structures and therefore the potential to illicit a good protective long term immunity should be higher.

The term attenuating mutation and the like refers to any genetic lesion in a gene which renders the gene non-functional. This may be, for example, by deletion of all or part of the gene, point mutation in the coding sequence resulting in a truncated gene product unable to carry out the normal function of the gene, or insertion or interruption of the gene by a nucleotide element which prevents the gene product being coded or causes any gene product generated to be such that it cannot carry out the normal function of the gene.

A mutation introduced into an attenuated bacterium of the invention would generally be a non-reverting attenuating mutation. Non-reverting means that for practical purposes the probability of the mutated gene being restored to its normal function is small, for example, less than 1 in $10^6$ preferably less than 1 in $10^9$ or more preferably less than 1 in $10^{22}$. The attenuated mycobacteria of the invention may be isolated form. This is usually desirable when the bacteria are to be used for the purposes of vaccination. The term "isolated" means that the bacteria are in a form in which they can be cultured, processed or otherwise used in a form which can be readily identified and in which it is substantially uncontaminated by other bacterial strains, for example, non-attenuated parent strains or unrelated bacterial strains. The term "isolated bacterium" thus encompasses cultures of a bacterial mutant of the invention, for example, in the form of colonies on a solid medium or in the form of a liquid culture, as well as frozen or dried preparations of the strain.

In a preferred aspect the attenuated mycobacterium is formed by insertion of an insertion element into the mpa gene. The insertion element may consist of a sequence of one or more, preferably ten or more, nucleotides. In preferred attenuated mycobacteria the mpa gene is attenuated by insertion of a known insertion element, for example, an IS21-like element, more preferably by insertion of the insertion element IS1612 or an insertion element at least 75% homologous to it. Most preferably the insertion of the IS1612 element or its homologue occurs at the target site 5'-ATGCAC-3' between nucleotides 202 and 209 of the mpa sequence. The mycobacteria which is attenuated is preferably MAP.

The attenuated mycobacterium may further comprise at least one additional mutation. This may be a mutation in a gene responsible for the production of products essential to bacterial growth which are absent in a human or animal host. For example, mutations to the gene for aspartate semi-aldehyde dehydrogenase (asd) have been proposed for the production of attenuated strains of *salmonella*. The asd gene is described further in Gene (1993) 129, 123-128. A lesion in the asd gene, encoding the enzyme aspartate B-semialdehyde dehydrogenase would render the organism auxotrophic for the essential nutrient diaminopelic acid (DAP), which can be provided exogenously during bulk culture of the vaccine strain. Since this compound is an essential constituent of the cell wall for gram-negative and some gram-positive organisms and is absent from mammalian or other vertebrate tissues, mutants would undergo lysis after about three rounds of division in such tissues. Analogous mutations may be made to the attenuated mycobacteria of the invention. Such mutations may also include disabling genes of the GS element including gsc and gsd.

In addition or in the alternative, the attenuated mycobacteria may carry a recA mutation. The recA mutation knocks out homologous recombination—the process which is exploited for the construction of the mutations. Once the recA mutation has been incorporated the strain will be unable to repair the constructed deletion mutations. Such a mutation will provide attenuated strains in which the possibility of homologous recombination to with DNA from wild-type strains has been minimized. RecA genes have been widely studied in the art and their sequences are available. Further modifications may be made for additional safety.

The invention further provides a process for preparing a vaccine composition comprising an attenuated bacterium according to the invention process comprises (a) inoculating a culture vessel containing a nutrient medium suitable for growth of said bacterium; (b) culturing said bacterium; (c) recovering said bacteria and (d) mixing said bacteria with a pharmaceutically acceptable diluent or carrier.

The mpa gene can also be inactivated by methods known in the art including other transposon mutagenesis, and allelic exchange.

Attenuated mycobacterial strains according to the invention may be constructed using recombinant DNA methodology which is known per se. In general, bacterial genes may be mutated by a process of targeted homologous recombination in which a DNA construct containing a mutated form of the gene is introduced into a host bacterium which it is desired to attenuate. The construct will recombine with the wild-type gene carried by the host and thus the mutated gene may be incorporated into the host genome to provide a bacterium of the present invention which may then be isolated.

The mutated gene may be obtained by introducing deletions into the gene, e.g by digesting with a restriction enzyme which cuts the coding sequence twice to excise a portion of the gene and then religating under conditions in which the excised portion is not reintroduced into the cut gene. Alternatively frame shift mutations may be introduced by cutting with a restriction enzyme which leaves overhanging 5' and 3' termini, filling in and/or trimming back the overhangs, and religating. Similar mutations may be made by site directed mutagenesis. These are only examples of the types of techniques which will readily be at the disposal of those of skill in the art.

Various assays are available to detect successful recombination. In the case of attenuations which mutate a target gene necessary for the production of an essential metabolite or catabolite compound, selection may be carried out by screening for bacteria unable to grow in the absence of such a compound. Bacteria may also be screened with antibodies or nucleic acids of the invention to determine the absence of production of a mutated gene product of the invention or to confirm that the genetic lesion introduced—e.g. a deletion— has been incorporated into the genome of the attenuated strain. In addition, GPL sugars may be extracted and analysed by high pressure liquid chromatography and other methods such as TLC known in the art.

The concentration of the attenuated strain in the vaccine will be formulated to allow convenient unit dosage forms to be prepared. Concentrations of from about $10^4$ to $10^9$ bacteria per ml will generally be suitable, e.g. from about $10^5$ to $10^8$ such as about $10^6$ per ml. Live attenuated organisms may be administered subcutaneously or intramuscularly at up to $10^8$ organisms in one or more doses, e.g from around $10^5$ to $10^8$, e.g about $10^6$ or $10^7$ organisms in a single dose.

The vaccines of the invention are conventionally administered parenterally, by injection, for example, either subcutaneously or intramuscularly. Additional formulations which are suitable for other modes of administration such as ingestion, rectal installation, or mucosally by inhalation. For suppositories, traditional binders and carriers may include, for example, polyalkylene glycols or triglycerides; such suppositories may be formed from mixtures containing the active ingredient in the range of 0.5% to 10%, preferably 1%-2%. Oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders and contain 10%-95% of active ingredient, preferably 25%-70%. Oral formulations may include enteric coatings so that vaccines are preferentially released in the small intestine or colon.

The proteins may be formulated into the vaccine as neutral or salt forms. Pharmaceutically acceptable salts include the acid addition salts (formed with free amino groups of the peptide) and which are formed with inorganic acids such as, for example, hydrochloric or phosphoric acids, or such organic acids such as acetic, oxalic, tartaric, maleic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The vaccines are administered in a manner compatible with the dosage formulation, and in such amount as will be prophylactically and/or therapeutically effective. The quantity to be administered, which is generally in the range of 500 µg to 5 mgs of antigen per dose, depends on the subject to be treated, capacity of the subject's immune system to synthesize antibodies, mode of administration and the degree of protection desired. Precise amounts of active ingredient required to be administered may depend on the route of administration or on judgement of the practitioner and may be peculiar to each subject.

The vaccine may be given in a single dose schedule, or preferably in a multiple dose schedule. A multiple dose schedule is one in which a primary course of vaccination may be with 1-10 separate doses, followed by other doses given at subsequent time intervals required to maintain and or reinforce the immune response, for example, at 1-4 months for a second dose, and if needed, a subsequent dose(s) after several months. The dosage regimen will also, at least in part, be determined by the need of the individual and be dependent upon the judgement of the practitioner.

The vaccines of the invention may be administered to recipients to treat established diseases or in order to protect them against diseases caused by the corresponding wild type mycobacteria such as inflammatory diseases such as Crohn's disease or sarcoidosis in humans of Johne's disease in animals. The vaccine may be administered by any suitable route as described above.

The invention is now illustrated by the following Examples which should be construed as non-limiting.

Examples

Characterisation of the mpa Gene

PCR performed on MAP DNA using a number of polynucleotide primers derived from the sequence of GS within *M. avium* sub sp. *silvaticum* (PCT/GB96/03221) failed to yield products with MAP. Although the first 209 nucleotides of mpa are present in *M. avium* subsp. *silvaticum*, the existence of an open reading frame was not apparent because the sequence was truncated in *M. avium* subsp. *silvaticum* by the IS21-like element, now designated IS1612. Primers including those from within IS1612 that were predicted to produce an amplification product and disclose further DNA sequences from within MAP, if this were the same as *M. avium* subsp. *silvaticum*, did not work. The genomic organisation of MAP in this region was found to be very different from that of *M. avium* subsp. *silvaticum*. Furthermore, the full extent of the IS21-like element (IS1612) in *M. avium* subsp. *silvaticum* remained unknown. When further experimentation disclosed the full sequence of IS1612 in *M. avium* subsp. *silvaticum*, primers selected on the basis of this new information again failed to give an amplification product, and reveal further DNA sequence of MAP. It became clear that a DNA sequencing strategy for this region of MAP, down stream of the GS element known in the art, based upon the DNA sequence information from *M. avium* subsp. *silvaticum* would not work.

In a new strategy, we used the enzymes Bam HI, SalI, PstI and XhoI and a variety of primers selected from the last known 150 bp of DNA sequence in this region of MAP, to obtain amplification products from MAP DNA using inverse PCR. This involved recircularisation of genomic digest and subsequent amplification by a set of 'inward' and 'outward' primers. The results were at first difficult to assess because of the production of a number of non-specific amplification products. In several experiments using this strategy however, one band of 280 bp was consistently obtained. This suggested that at least one of the primers in the reaction was specific for further sequence of MAP. This 280 bp product was therefore selected from amongst the other amplification products for a further round of cloning and DNA sequencing. This resulted in our obtaining 250 bp of sequence from within the mpa gene of MAP. Further work revealed that MAP did not contain an IS21-like element (IS1612) found in GS in *M. avium* subsp. *silvaticum*. It became clear that the mpa gene existed downstream of the GS element in MAP. Using inverse PCR the entire sequence of the mpa gene (SEQ ID No. 1) and the mpa polypeptide which it encodes (SEQ ID No. 2) were obtained and verified by sequencing both strands. Comparison of the sequence of the polypeptide in SEQ ID No. 2 with existing amino acid sequences available in the databases, demonstrated homologies which revealed the function of the mpa gene product to be an acetyl transferase closely linked with pathogenicity in other organisms.

Functional Characterisation of mpa.

Sequence data for mpa was compared against known sequences using the BLASTN 1.4.11 [24 Nov. 1997] [Build 24 Nov. 1997] search facility at NCBI (website: ncbi[dot]nlm [dot]nih[dot]gov[slash] genbank[slash]) on GenBank Flat File release 105.0 (release date 15 Feb. 1998). Homologues to mpa were found in acetylases from *S. typhimurium, S. flexneri* and *R. leguminosarum*. The function of this ORF as an acetylase is strengthened by its very high similarity in hydrophobicity plots of homologues (see FIG. 1).

In each of these cases the acetylase gene is crucial for determining the host specificity of the organism. Acetylation of lipopolysaccharide O-antigen by the oac gene, carried by a strain specific bacteriophage, converts *S. flexneri* to the more virulent 06 serotype (Clark C A, Beltrame J & Manning P A. Gene 107: 43-52. 1991). Critical mutations or deletions in the oafA gene, which causes the acetylation of the exported O-antigen lipopolysaccharide in *S. typhimurium*, destroys an epitope crucial for O5 serotype antibody binding and decreases the virulence of this bacteria for host cells (Slauch J M, Lee A A, Mahan M J & Mekalanos J J. J. Bacteriol. 178: 5904-5909.1996). An mpa homologue nodX is not present in all species of *Rhizobium*, however when present it causes the nod to be acetylated. This specific modification allows the strain to increase the range of hosts that it can stimulate to nodulate. Nod factors consist of polysaccharides that contain glucose, galactose and fucose residues which are methylated and sometimes acetylated. In mycobacteria also, acetylation of GPL's can be important for host recognition. De-acetylation of the terminal fucose of GPL's from *M. avium* MAC serotype 9 abolishes rabbit anti-serotype 9 antibody agglutination indicating that acetylation plays a key role in strain variability amongst bacteria and may be directly attributable as a virulence factor. In *M. avium* serotype 2, transposon knockouts causing specific GPL to alter terminal sugar derivatisation including acetylation, abolishes pathogenicity. Acetylation of rhamnose in GPL's of *Mycobacterium smegmatis* induces resistance to mycobacteriophage D4 by inducing conformational changes that destroy the phage attachment site. Thus in MAP, the mpa gene is responsible for modification of terminal sugar residues in MAP GPL's which are critically important in determining cell surface recognition and receptor binding and are important determinants of pathogenicity. *M. avium* subsp. *silvaticum* differs from MAP in this important respect because the mpa gene in *M. avium* subsp. *silvaticum* is interrupted by the insertion of IS1612. The use of IS1612 using standard transfection methodologies to knock-out mpa in MAP produces an attenuated mutated strain. The introduction of such specific mutations, including those in the mpa gene, is of use in the provision of attenuated vaccine strains of MAP to increase the resistance of animals and humans to infections caused by this organism. Transfection of the mpa gene from MAP into a recipient bacterium particularly accompanied by the simultaneous transfection of GS will confer on the recipient the property of synthesising cell surface structures which mimic those of mpa and thus also serve as a vaccine to increase the resistance of animals and humans to MAP infections.

Transformation of Another Bacterium by mpa.

Mpa specific primers are designed with concatenated SadI sites in p12 and a PstI site in p13 at the 3' ends (P12: AGC-GAGCTCACGTGACTGAAGCC (SEQ ID NO:6); P13: GCTCTGCAG CCGGAACACAACGC (SEQ ID NO:7)). A 1371 bp PCR product is amplified, purified by gel electrophoresis and cleaned with Qiagen gel clean column. The product is then cloned into T-Vector (Promega) and transformed into *E. coli*. The plasmid is grown up, purified and a PstI insert fragment removed and purified as before. This is subcloned into a mycobacterial shuttle vector. This vector contains a mycobacterial ori, *E. coli* ori, hygromycin antibiotic marker and the hsp60 promoter immediately upstream of the insertion locus. The resulting construct is transformed into *E. coli* and purified to 1 mg/ml. This vector is then sequenced to check that the PCR step and cloning steps do not introduce errors into the sequence and that the sequence is inserted in the correct orientation in the vector. *M. smegmatis* (strain MC$^2$155) is grown into exponential phase, washed twice in 10% glycerol and diluted to OD260:0.5 in TE x1 (Tris 10 mM EDTA 0.1 mM). 1 µg of plasmid is added and the mixture pulsed at 1000Ω:2.5 kV:25 fD using a BioRad electroporation unit. Cells are recovered in 500 µl SOC (2 g Tryptone, 0.5 g Yeast extract, 1 ml 1M NaCl, 0.25 ml 1M KCl, 1 ml Mg Salts, 1 ml 2M Glucose) at 37° C. for 3 hours and then plated onto Middlebrooks 7H11:45 µg/ml Hygromycin selection plates. Transformants are selected and mpa presence checked by mpa specific P12/P13 PCR. Expression of mpa is also checked by making total mRNA preps of transformants in exponential growth phase. This is done by pelleting a 4 day 30 ml culture (in Middlebrooks 7H11:45 µg/ml Hygromycin broth) at 3,000×g for 20 minutes. This is resuspended in 200 µl RNAse free water and transferred to a ribolyser tube containing silica beads. 500 µl of DSA solution (Divolab No. 1:9.6 ml, 500 mM Na Acetate (pH4.0) 24 ml, RNAse free water 66.4 ml) 500 µl Acid Phenol (Water saturated phenol with Na Acetate at pH4.0) and 100 µl chloroform/isoamyl alcohol (24:1). This is then ribolysed at a speed setting of 6.5 for 45 secs. The tubes are then microfuged for 10 minutes at 13,000×g. Total mRNA is extracted with equal volume of chloroform/isoamyl alcohol and then precipitated at −70° C. with isopropanol for 2 hours. This is then microfuged at 13,000×g for 20 minutes dried and resuspended in RNAase free water. Samples are treated with DNAase and then cDNA produced using the P12 primer as template with SuperscriptII Reverse Transcriptase (Gibco-BRL). PCR using P12/P13 primers is then performed showing bands of the correct size. Controls without DNAase and with RNAase H treatment are performed in parallel. This demonstrates transcribed copies of mpa present in *M. smegmatis*. Translation is revealed by taking exponential growth cultures of transformants and whole cell lysates using 1 minute sonication in 2% SDS-PAGE buffer. These whole cell protein extracts are then electrophoresed on 1% polyacrylamide gels and western blotted onto nylon membranes. These are then hybridised with rabbit raised, mpa peptide antisera and developed with anti-rabbit HRP conjugate/ECL peroxide system.

Deactivation of mpa in MAP Using IS1612

General transposon mutagenesis of MAP can be achieved using Tn-Mut.Vectors. These vectors contain the insertion sequence, a kanamycin selection marker, shuttle vector origins of replication (including a thermosensitive Myc-ori) and the counterselectable suicide marker sacB, and are of proven ability in the mutagenesis of BCG, *M. tuberculosis, M. phlei* and *M. smegmatis*. Selected drug resistant transformants may be screened for interruption of the mpa gene. However, we have shown that mpa in *M. avium* subsp. *silvaticum* is interrupted by the insertion at a specific site of IS1612 and that MAP does not contain IS1612 and its mpa gene is intact. IS1612 cloned from a clinical isolate of *M. avium* subsp. *silvaticum* or IS1612-containing mycobacterium can be used in a suitable construct for the specific inactivation of mpa in MAP. Previous studies have shown that IS21-like elements resembling IS1612 can have a selected DNA marker inserted into a region immediately downstream of the istB gene without losing transpositional activity. Using primer mutagenesis a unique restriction site is created 4 bp downstream of IS16121 istB. A hygromycin selection marker is inserted into this site and the resultant transposon substituted into the Tn-Mut vector in place of 151096. This vector is introduced by electroporation into MAP or a pathogenic *M. avium* containing mpa, and successful transformants isolated using the selection and counterselection markers and thermotolerant conditions 30° C. Cultures are subbed at intervals into 2% sucrose media and grown at a non-permissive temperature (37° C.). The selection marker is co-transferred with the insertion element and selects for transpositional events whilst the temperature suppresses plasmid replication, inducing plasmid leaching and killing plasmid positives via sacB expression. DNA extracted from clones is screened using a gene specific primer and an insertion sequence specific primer. Cloned PCR products are sequenced and checked against known target sequence data. Clones are then cultured and RFLP analysis performed using insertion sequence specific probes to determine insertion frequency. Clones with insertions in the mpa gene are selected for use as candidate vaccine strains with attenuated pathogenicity.

The invention claimed is:

1. An expression vector which comprises:
   (a) a polynucleotide comprising the entire nucleotide sequence set out in SEQ ID NO. 1 or the complement thereof; or
   (b) a polynucleotide that encodes a polypeptide that comprises:
      (i) the sequence set out in SEQ ID NO: 2;
      (ii) the polypeptide encoded by nucleotides 210-1335 of SEQ ID NO: 1;
      (iii) amino acids 158-211 of SEQ ID NO: 2; or
      (iv) amino acids 380-444 of SEQ ID NO: 2,
   wherein said polypeptide has the ability to stimulate an immune response against the polypeptide of SEQ ID NO: 2;
   operably linked to regulatory sequences capable of directing expression of said polynucleotide in a host cell.

2. A vector according to claim 1 which is a plasmid or viral vector and wherein said polynucleotide is under control of a promoter.

3. A plasmid according to claim 2, wherein the promoter is a CMV, MMLV, RSV or SV40 promoter.

4. An isolated non-pathogenic microorganism or a cell isolated from a human or animal species prone to infection by *Mycobacterium avium* subspecies *paratuberculosis* (MAP) which has been transformed or transfected with a nucleic acid construct comprising a polynucleotide selected from:
   (a) a polynucleotide comprising the entire nucleotide sequence set out in SEQ ID NO: 1 or the complement thereof; or
   (b) a polynucleotide which encodes a polypeptide comprising:
      (i) the sequence set out in SEQ ID NO: 2;
      (ii) the polypeptide encoded by nucleotides 210-1335 of SEQ ID NO: 1;
      (iii) amino acids 158-211 of SEQ ID NO: 2; or
      (iv) amino acids 380-444 of SEQ ID NO: 2;
   wherein said polypeptide has the ability to stimulate an immune response against the polypeptide of SEQ ID NO: 2,
   or a vector as defined in claim 2.

5. An isolated non-pathogenic microorganism according to claim 4 which is a recombinant bacterium or virus.

6. An isolated non-pathogenic microorganism or a cell according to claim 4, wherein the nucleic acid construct further comprises a polynucleotide which encodes the polypeptides of the GS region of MAP.

7. An isolated non-pathogenic microorganism or a cell according to claim 4, wherein the gene or genes present in the nucleic acid construct are expressed.

8. An isolated polynucleotide selected from:
   (a) a polynucleotide comprising the entire nucleotide sequence set out in SEQ ID No. 1 or the complement thereof; or
   (b) a polynucleotide which encodes the polypeptide of SEQ ID NO: 2,
   wherein said polynucleotide encodes a polypeptide that has the ability to stimulate an immune response against the polypeptide of SEQ ID NO: 2.

* * * * *